(12) United States Patent
Bodén Wästfält et al.

(10) Patent No.: US 6,299,879 B1
(45) Date of Patent: Oct. 9, 2001

(54) METHODS OF IMMUNIZATION BY ADMINISTERING FIBRINOGEN BINDING PROTEIN OR FRAGMENTS THEREOF

(75) Inventors: Maria K. Bodén Wästfält, Lund; Jan-Ingmar Flock, Bromma, both of (SE)

(73) Assignee: Alfa Laval Agri International Aktiebolag (SE)

( * ) Notice: Subject to any disclaimer, the term of this patent is extended or adjusted under 35 U.S.C. 154(b) by 0 days.

(21) Appl. No.: 09/276,141

(22) Filed: Mar. 25, 1999

Related U.S. Application Data

(62) Division of application No. 08/244,229, filed as application No. PCT/SE93/00759 on Sep. 20, 1993, now abandoned.

(30) Foreign Application Priority Data

Sep. 21, 1992 (SE) .................................................... 9202720
Sep. 13, 1993 (SE) .................................................... 9302955

(51) Int. Cl.[7] .......................... A01K 37/18; A61K 39/00; A61K 39/38; A61K 39/40; C07K 1/00
(52) U.S. Cl. .................. 424/185.1; 530/350; 530/387.1; 424/130.1; 424/164.1; 424/184.1; 514/2
(58) Field of Search ................................. 530/350, 387.1; 514/2; 424/130.1, 185.1, 164.1, 184.1

(56) References Cited

U.S. PATENT DOCUMENTS 5,189,015  2/1993  Höök et al. .

OTHER PUBLICATIONS

Foster TJ. Potential for vaccination against infections caused by *staphylococcus aureus*. Vaccine 9:221–227, 1991.*
Boden MK and Flock J–I. Fibrinogen–binding protein/clumping factor from *Stapylococcus aureus*. Infection and immunity 57:2358–2363, 1989.*
M.K. Boden et al., "Evidence for Three Different Fibrinogen–Binding Proteins with Unique Properties form *Staphylococcus Aureus* Strain Newman", *Microbial Pathogenesis* 12:289–298 (1992).
Boden M.K., Flock J.I., "Cloning and Characterization of a Gene for a 19 kDa Fibrinogen–binding Protein as *Aureus*", Mol. Microbiol. 12:599–606 (1994) Medline 95020594.

* cited by examiner

Primary Examiner—Gary L. Kunz
Assistant Examiner—Robert S. Landsman
(74) Attorney, Agent, or Firm—Burns, Doane, Swecker & Mathis, L.L.P.

(57) ABSTRACT

The present invention provides a method for immunizing a mammal against Staphylococcus infection comprising administering to that mammal a protein or fragment thereof comprising the amino acid sequence:

(SEQ ID NO:8)
SEGYGPREKK PVSINHNIVE YNDGTFKYQS RPKFNSTPKY

IKFKHDYNIL EFNDGTFEYG ARPQFNKPAA KTDATIKKEQ

KLIQAQNLVR EFEKTHTVSA HRKAQKAVNL VSFEYKVKKM

VLQERIDNVL KQGLVR, or a fragment thereof retaining that portion of the sequence responsible for fibrinogen binding activity.

4 Claims, 10 Drawing Sheets

```
  1 GACTAGTGTATAAGTGCTGATGAGTCACAAGATAGATAACTATATTTTGTCTATATTATA  60
                                               -35
 61 AAGTGTTTATAGTTAATTAATAATTAGTTAATTTCAAAAGTTGTATAAATAGGATAACTT 120
                       -18            -35
121 AATAAATGTAAGATAATAATTTGGAGGATAATTAACATGAAAAATAAATTGATAGCAAAA 180
        -18                             M  K  N  K  L  I  A  K

181 TCTTTATTAACAATAGCGGCAATTGGTATTACTACAACTACAATTGCGTCAACAGCAGAT 240
     S  L  L  T  I  A  A  I  G  I  T  T  T  T  I  A  S  T  A  D

241 GCGAGCGAAGGATACGGTCCAAGAGAAAAGAAACCAGTGAGTATTAATCACAATATCGTA 300
     A↑ S  E  G  Y  G  P  R  E  K  K  P  V  S  I  N  H  N  I  V

301 GAGTACAATGATGGTACTTTTAAATATCAATCTAGACCAAAATTTAACTCAACACCTAAA 360
     E  Y  N  D  G  T  F  K  Y  Q  S  R  P  K  F  N  S  T  P  K

361 TATATTAAATTCAAACATGACTATAATATTTTAGAATTTAACGATGGTACATTCGAATAT 420
     Y  I  K  F  K  H  D  Y  N  I  L  E  F  N  D  G  T  F  E  Y

421 GGTGCACGTCCACAATTTAATAAACCAGCAGCGAAAACTGATGCAACTATTAAAAAAGAA 480
     G  A  R  P  Q  F  N  K  P  A  A  K  T  D  A  T  I  K  K  E

481 CAAAAATTGATTCAAGCTCAAAATCTTGTGAGAGAATTTGAAAAAACACATACTGTCAGT 540
     Q  K  L  I  Q  A  Q  N  L  V  R  E  F  E  K  T  H  T  V  S

541 GCACACAGAAAAGCACAAAAGGCAGTCAACTTAGTTTCGTTTGAATACAAAGTGAAGAAA 600
     A  H  R  K  A  Q  K  A  V  N  L  V  S  F  E  Y  K  V  K  K

601 ATGGTCTTACAAGAGCGAATTGATAATGTATTAAAACAAGGATTAGTGAGATAATACTTC 660
     M  V  L  Q  E  R  I  D  N  V  L  K  Q  G  L  V  R  *

661 TGTCATTATTTTAAGTTCAAAATAATTTAATATTATATTATTTTTTATTAATAAAACGAC 720

721 TATGCTATTTAATGCCAGGTTAATGTAACTTTCCTAAAATTGACTATATAATCGTTAAGT 780

781 ATCAATTTTAAGGAGAGTTTACAATGAAATTTAAAAAAATATATATTAACAGGAACATTAG 840
                         M  K  F  K  K  Y  I  L  T  G  T  L  A

841 CATTACTTTTATCATCAACTGGGATAGCAACTATAGAAGGGAATAAAGCAGATGCAAGTA 900
     L  L  L  S  S  T  G  I  A  T  I  E  G  N  K  A  D  A  S  S

901 GTCTGGACAAATATTTAACTGAAAGTCAGTTTCATGATAAACGCATAGCAGAAGAATTAA 960
     L  D  K  Y  L  T  E  S  Q  F  H  D  K  R  I  A  E  E  L  R

961 GAACTTTACTTAACAAATCGAATGTATATGCATTAGCTGCAGGAAGCTT 1009
     T  L  L  N  K  S  N  V  Y  A  L  A  A  G  S    1
```

FIG. 3

```
  1 ATAGATAACTATATTTTGTCTATATTATAAAGTGTTTATAGTTAATTAATAATTAGTTAA  60
  1         G         CA                                            60

61 TTTCAAAAGTTGTATAAATAGGATAACTTAATAAATGTAAGATAATAATTTGGAGGATAA 120
 61                                                              120

121 TTAACATGAAAAATAAATTGATAGCAAAATCTTTATTAACAATAGCGGCAATTGGTATTA 180
121      G           GC                 T              A          180

181 CTACAACTACAATTGCGTCAACAGCAGATGCGAGCGAAGGATACGGTCCAAGAGAAAAGA 240
181                                                              240

241 AACCAGTGAGTATTAATCACAATATCGTAGAGTACAATGATGGTACTTTTAAATATCAAT 300
241                                                              300

301 CTAGACCAAAATTTAACTCAACACCTAAATATATTAAATTCAAACATGACTATAATATTT 360
301                                                              360

361 TAGAATTTAACGATGGTACATTCGAATATGGTGCACGTCCACAATTTAATAAACCAGCAG 420
361                                                              420

421 CGAAAACTGATGCAACTATTAAAAAAGAACAAAAATTGATTCAAGCTCAAAATCTTGTGA 480
421                                                              480

481 GAGAATTTGAAAAAACACATACTGTCAGTGCACACAGAAAAGCACAAAAGGCAGTCAACT 540
481                                                              540

541 TAGTTTCGTTTGAATACAAAGTGAAGAAAATGGTCTTACAAGAGCGAATTGATAATGTAT 600
541                                                              600

601 TAAAACAAGGATTAGTGAGATAATACTTCTGTCATTATTTTAAGTTCAAAA....TAATT 660
601          T A    A       AA   C  GC G T TC GG     TAAT         660

661 TAATATTATATTATTTTTTATTAATAAAACGACTATGCTATTTAATGCCAGGTTAATGTA 720
661 A    G     G A     G      G   AA G AT          A             720

721 ACTTTCCTAAAATTGACTATATAATCGTTAAGTATCAATTTTAAGGAGAGTTTACAATGA 780
721 T G               C  AG                     C T              780

781 AATTT 785
781       785
```

FIG. 4

```
  1 MKNKLIAKSLLTIAAIGITTTTIASTADASEGYGPREKKPVSINHNIVEYNDGTFKYQSR  60
  1      A     L                                                 60

61 PKFNSTPKYIKFKHDYNILEFNDGTFEYGARPQFNKPAAKTDATIKKEQKLIQAQNLVRE 120
 61                                                              120

121 FEKTHTVSAHRKAQKAVNLVSFEYKVKKMVLQERIDNVLKQGLVR 165
121                                         K    165
```

FIG. 5

Fbg-bp, strain Newman:

SEGYGPR

EKKPVSINH  NIVEYNDGSFK  YQSRPKFNSTP
KYIKFKHDY  NILEFNDGTFE  YGARPQFNKPA

AKTDATIKKEQKLIQAQNLVREFEKTHTVSAHRKAQKAVNLVSFEYKVKKMVLQERIDNVLKQGLVR

Coagulase, strain 8325-4:

(C-terminal fragment)

```
                      ASQ          YGPRPQFNKTP
KYVKYRDAGT  GIREYNDGTFG  YEARPRFNKPS
     ETNAY  NVTTHANGQVS  YGARPTYKKPS
     ETNAY  NVTTHANGQVS  YGARPTQNKPS
     KTNAY  NVTTHGNGQVS  YGARQAQNKPS
     KTNAY  NVTTHANGQVS  YGARPTYKKPS
     KTNAY  NVTTHADGTAT  YGPRVTK
```

FIG. 6

METHODS OF IMMUNIZATION BY ADMINISTERING FIBRINOGEN BINDING PROTEIN OR FRAGMENTS THEREOF

This application is a divisional of application Ser. No. 08/244,229, filed Dec. 9, 1994 which is a 371 of PCT/SE93/00759 filed Sep. 20, 1993 now abandoned.

DESCRIPTION

TECHNICAL FIELD

The present invention relates to fibrinogen binding proteins. Further the invention relates to pharmaceutical compositions and method for treatment.

The object of the present invention is to obtain fibrinogen binding proteins.

A further object is to obtain said protein by means of genetic engineering technique by using, e.g. a plasmid comprising a nucleotide sequence coding for said protein.

BACKGROUND OF THE INVENTION

Clumping of *Staphylococcus aureus* in plasma has been suggested as a potential virulence factor.[1-5] Several mechanisms can be responsible for this aggregation. A fibronectin-binding protein has been suggested to cause aggregation of staphylococci in fibronectin at the concentration found in sera.[5,6] The presence of protein A causes staphylococci to aggregate in normal human sera, which frequently contain specific immunoglobulins directed against staphylococcal antigens.[7] Due to a high cell surface hydrophobicity, many staphylococcal strains auto-regulate under isotonic conditions.[8] It is believed that clumping of staphylococci in fibrinogen is caused by the so called clumping factor or fibrinogen-binding protein, situated on the staphylococcal cell surface.[1,9] Fibrinogen has also been suggested to mediate adhesion of *S. aureus* to cultured human endothelial cells[10] and to catheters in vitro and in vivo.[11,12] It has been disputed whether clumping factor is distinct from coagulase[1] or if it is a cell-bound form of coagulase.[13, 14] *Staphylococcus aureus* coagulases can be grouped into eight different serotypes[15] and the existence of multiple molecular forms of coagulases has been suggested,[16] although most investigators believe that lower molecular weight subspecies in coagulase preparations are due to proteolytic degradation of a larger protein.[17] Staphylococcal coagulases have been shown to induce polymerization of fibrinogen to fibrin by binding, and thereby activating, prothrombin. The coagulase-prothrombin complex causes the release of fibrinopeptides from fibrinogen in a manner similar to that described for thrombin in physiological blood clotting.[18] Fibrinogen precipitation and network formation can also be induced non-enzymatically, e.g. by exposing fibrinogen to various highly positively charged molecules like protamine, which interacts with specific negatively charged sites on the D-domain of fibrinogen.[19]

We have recently described staphylococcal components that interact with fibrinogen and which can be purified from *S. aureus* culture supernatants.[13] These are an 87 kDa coagulase and a 19 kDa fibrinogen-binding protein. The 87 and 19 kDa fibrinogen-binding proteins are essentially extracellular proteins, but can to some extent be found on the staphylococcal cell surface. Thus, these proteins can give rise to the clumping phenomenon both by inducing coagulation and by direct fibrinogen-binding.

In this report we show that there are at least three distinct fibrinogen-binding proteins produced by *S. aureus* strain Newman, and that two of these proteins are coagulases.

Results

SDS-PAGE analysis of fibrinogen binding-proteins produced at different times during staphylococcal cell growth

*Staphylococcus aureus* strain Newman was grown in BHI or LB and samples were taken every hour for 14 h. Culture supernatants were applied onto fibrinogen-Sepharose and the eluted material was analysed on Coomassie blue-stained SDS-PAGE gels. FIG. 1 shows fibrinogen-binding proteins from culture supernatants of staphylococci grown in LB under low aeration conditions. Under these conditions, an 87 kDa protein was produced in large amounts, mainly during the first 7 h and a 60 kDa protein appeared after 5–6 h and was produced in large amounts after 9 h of growth. Under high aeration conditions, the 87 kDa protein was produced in lower amounts and the switch to production of the 60 kDa protein accurred after only 3 h resulting in a higher production of 60 kDa protein compared to when less air was supplied to the culture. Using a rich medium like BHI, and the same high aeration conditions, this switch again accurred after 7 h (data not shown). In all cultures, the 87 kDa protein was produced mainly during the exponential growth phase and the 60 kDa protein mainly during the post-exponential growth phase. The switch from production of the 87 kDa protein to production of the 60 kDa protein reflected the nutritional status, rather than the optical density of the culture. A 19 kDa protein was produced constitutively during these 14 h of growth (FIG. 1).

SDS-PAGE, affinity- and immuno-blot analysis of affinity purified proteins

*Staphylococcus aureus* grown in BHI for 3–4 h produced the 87 and 19 kDa proteins but no detectable 60 kDa protein. Such culture supernatants were applied onto fibrinogen-Sepharose in order to purify the 87 and 19 kDa proteins. Similarly, culture supernatants from *S. aureus* grown in LB for 6–8 h, containing predominantly the 60 kDa protein but also the 87 and 19 kDa proteins, were used to purify the 60 kDa protein. The crude material was first passed over fibrinogen-Sepharose, in order to eliminate the 87 and 19 kDa proteins, and the effluent (containing the 60 kDa protein which also bound to fibrinogen-Sepharose, but to a lower extent than the 87 and 19 kDa proteins) was applied onto prothrombin-Sepharose. The 87 and 19 kDa proteins did not bind to prothrombin-Sepharose. Eluted material from affinity purifications was subjected to SDS-PAGE and affinity-blot analysis (FIG. 2). These blots were probed with fibrinogen or prothrombin, followed by rabbit antifibrinogen or rabbit antiprothrombin sera which had been pre-incubated with *S. aureus* culture supernatants in order to absorb naturally occuring antistaphylococcal antibodies. It could thus be shown that the 87 and 19 kDa proteins bound only to fibrinogen and not to prothrombin, while the 60 kDa protein bound both fibrinogen and prothrombin. Controls were performed by incubating filters with only pre-absorbed primary antibody, omitting fibrinogen and prothrombin (data not shown). In these controls, no 87, 60 or 19 kDa proteins were detected. By using a dilution series both of antigen and fibrinogen or prothrombin, it was shown that the binding reactions were specific and not the result if contaminating blood proteins in the fibrinogen and prothrombin preparations. For example, 10 ng/ml of fibrinogen could detect 0.1 ng of the 87 or 60 kDa proteins in these affinity-blots. When 10 ng/ml of prothrombin was used in these tests, 0.1 ng 60-kDa protein could be detected, while a concentration of 10 µg/ml of prothrombin could not detect a 1 ng 87-kDa band (data not shown).

The anti-19 serum recognized not only the 19 kDa protein but also the 87 kDa protein and a 35 kDa protein (FIG. 3).

Furthermore, there was a close resemblance between blots incubated with fibrinogen followed by antifibrinogen antibody and blots incubated with anti-19 serum.

Antibodies to the 60 kDa protein seem to occur naturally among several mammalian species (e.g. rabbit, goat and man; data not shown). The anti-19 serum, as well as pre-immune serum from the same rabbit, showed some reactivity towards this 60 kDa protein. However, pre-absorption with 19 kDa protein completely abolished binding to the 19 and 35 kDa bands, but not to the 60 kDa band, while antiserum pre-absorbed with 60 kDa protein reacted with the 19 and 35 kDa bands but not with the 60 kDa band (FIG. 4).

Peptide mapping

Proteins were purified by a combination of affinity chromatography and preparative SDS-PAGE. The purity of these preparations was confirmed on silver stained SDS-PAGE gels (FIG. 5). Dimerisation of the 19 kDa protein into a 35 kDa protein could be detected on the silver stained gels. On affinity-blots, using fibrinogen and antifibrinogen antibodies, not only the 35 kDa dimer, but also bands of higher molecular weight were detected. Upon digestion with α-chymotrypsin, the dimerisation of the 19 kDa protein was disrupted, but the 19 kDa band was left intact. This protease did not have any apparent effect on the 87 kDa protein, whereas the fibrinogen-binding ability of the 60 kDa protein was completely lost after treatment with α-chymotrypsin. On the contrary, treatment of these proteins with staphylococcal V8 protease only partly digested the 60 kDa protein while the 87-kDa protein was digested into low molecular weight peptides (FIG. 5).

NH$_2$-terminal sequence analysis

Analyses of NH$_2$-terminal sequences revealed that the 87 kDa protein was related to previously described coagulases, while the 19 kDa protein had a unique NH$_2$-terminal sequence. The NH$_2$-terminal sequence of the 60 kDa coagulase was blocked (Table 1).

Coagulase test

Coagulase tests were performed with proteins purified by a combination of affinity chromatography and preparative SDS-PAGE. These preparations did not contain contaminations of other staphylococcal proteins as shown on silver stained SDS-PAGE gels (FIG. 5). The 87 and 60 kDa proteins coagulated rabbit plasma, while the 19 and 35 kDa proteins SEQ. ID NO: 1–6 produced a precipitate or a weak coagulase reaction in these.

TABLE 1

NH$_2$-terminal sequence analysis

| Staphylococcal strain | NH$_2$-terminal sequence |
|---|---|
| S. aureus BB | IVTKD YSKES RVNEN SKYGT |
| S. aureus 213 | IVTKD YSKES RVNEK SKKGA |
| S. aureus 8325-4 | IVTKD YSGKS QVNAG SKNGT |
| S. aureus Newman 87 kDa | IVTKD YSGKS QVNAG SKNGT |
| S. aureus Newman 60 kDa | — |
| S. aureus Newman 19 kDa | SEGYG PREKK PVSIN HNIVE |
| S. aureus Newman 35 kDa | M-Y- P-EKK PV- |

TABLE 2

Coagulase test

| | | Clotting at | | |
|---|---|---|---|---|
| Preparation | Inhibitor | 1 h | 2 h | 24 h |
| 87 kDa | — | + | + | + |
| 87 kDa | Aprotinin, PMSF, NEM, EDTA | + | + | + |
| 87 kDa | Heparin | − | + | + |
| 87 kDa | DFP | − | − | − |
| 60 kDa | — | + | + | + |
| 60 kDa | Aprotinin, PMSF, NEM, EDTA | + | + | + |
| 60 kDa | Heparin | − | + | + |
| 60 kDa | DFP | − | − | − | tests. Dilution series of the 87 and 60 kDa proteins showed that there was a dose-response relationship. To produce a positive reaction, 25 ng of the 60 kDa protein was required, while only 1 ng of the 87 kDa protein was needed to coagulate rabbit plasma within 24 h. The activities of the 87 and 60 kDa coagulases were not affected by the addition of the protease inhibitors NEM, EDTA, aprotinin and PMSF, to the rabbit plasma. In the presence of heparin, higher concentrations of both coagulases were needed for a positive reaction. Rabbit plasma containing the protease inhibitor DFP was not clotted by either coagulase (Table 2).

Identification of the 19 kDa fibrinogen-binding (fib) protein from strain FDA 486.

S. aureus strain FDA 486, which was the strain from which the library was obtained, was shown to express the 19 kDa fib protein. Affinity purified material from staphylococcal culture supernatants were analyzed in Western blots after SDS-PAGE separation (FIG. 1). The 19 kDa fibrinogen-binding protein expressed by the FDA 486 strain bound fibrinogen and the anti-fib serum, comparable to the protein purified from strain Newman.

Cloning of the fib gene in E. coli.

A genomic library containing DNA from S. aureus strain FDA 486 was screened with the anti-fib serum. A clone designated λfib-50 was isolated. This clone expressed a fibrinogen-binding protein of approximately 16 kDa, which bound anti-fib serum in a Western blot experiment. The fib gene was further subcloned into a pBluescript SK+vector (FIG. 2). Digestion of λfib-50 with HindIII generated 3 fragments containing staphylococcal DNA. One of these, contained by pBfibIII expressed the fibrinogen-binding protein (FIG. 1). The 2.4 kb insert in the pBfibIII plasmid was isolated and digested with XbaI, resulting in two fragments of 1.7 and 0.7 kb respectively. These fragments were subcloned into the pBluescript SK+vector as well as the M13mp18 and M13mp19 vectors (FIG. 2). Of the resulting plasmids and pBfibT was found to express a fibrinogen-binding protein which was slightly larger than the recombinant protein produced by the pBfibIII plasmid (FIG. 1).

The invention further comprises a microorganism containing at least one hybrid-DNA-molecule according to above. The plasmid pBfibIII in an E. coli XL has been deposited at the Deutsche Sammlung von Mikroorganismen (DSM), and has thereby obtained deposition number DSM . . .

Sequencing of the fib gene from S. aureus FDS 486.

The fib gene contained in the M13 constructs was sequenced by the Sanger dideoxy-chain termination method. The pBfibT plasmid was found to contain an open reading frame of 309 bp. The pBfibJ vector contained a putative TGGAGGA ribosomal binding site situated 15-9 base pairs upstream from the ATG start codon. Furhter upstream putative promoter sequences were identified. Computer assisted analysis revealed an open reading frame of 495 bp corresponding to 165 amino acids including a signal sequence of 29 amino acids. The first 23 amino acids in the mature protein were identical to the sequence obtained by $NH_2$-terminal analysis of the purified native protein. The predicted molecular mass of the fib protein is 15.9 kb. The complete nucleotide and deduced amino acid sequence is shown in FIG. 3.

Sequencing of the fib gene from *S. aureus* Newman.

Based on the DNA sequence obtained from the fib gene cloned from *S. aureus* FDA 486, primers were produced (FIG. 2). These primers were used to ampify the fib gene, both from strain FDA 486 and from strain Newman, using the polymerase chain reaction method. The resulting fragments were sequenced using fluorescent base terminators on an automatic sequenator. A comparison between the fib genes from these staphylococcal strains is shown in FIG. 4. The sequence from the cloned fib gene from *S. aureus* FDA 486 was confirmed using the same sequencing strategy. A comparison between the deduced amino acid sequences of the fib proteins from the two strains is shown in FIG. 5.

Computer assisted analysis of the fib gene sequence.

Using either the nucleotide or the amino acid sequence as a probe, no close similarity to any protein or nucleotide sequence in the University of Wisconsin Genetics Computer Group database was found. The protein showing the closest resemblance was coagulase from *S. aureus*. A sequence of 22 amino acids repeated twice with a spacing of 9 amino acids, located in the $NH_2$-terminal part of the mature protein showed homology to the COOH-terminal part of coagulase, where several 27 amino acids long repeats are situated (FIG. 6).

Discussion

We have previously described a 87 kDa fibrinogen-binding protein which exerts coagulase activity and is produced by *S. aureus* in culture supernatants.[13] We have suggested that this 87 kDa coagulase and a 19 kDa fibrinogen-binding protein, both of which are present on the cell surface, are involved in the clumping of *S. aureus* in fibrinogen. In this study we show that *S. aureus* strain Newman has two different types of coagulase secreted in a sequential manner during cell growth (FIG. 1). The 87 kDa coagulase was produced early during growth and was later replaced by the 60 kDa coagulase. The rate at which this switch occurred varied with growth rate and type of media used, i.e. under low aeration conditions or in a rich medium this switch was postponed (data not shown). This suggests that the presence of some environment factor(s) induces the production of the 87 kDa protein and suppresses 60 kDa protein production. It is likely that the 87 kDa coagulase is negatively regulated by the agr locus together with protein A.[20]

It was concluded from the results of the analyses by SDS-PAGE and immunoblotting of proteins purified by affinity chromatography that both the 60 and 87 kDa proteins bound fibrinogen, but only the 60 kDa protein bound prothrombin (FIG. 2). This is contradictory to our previous results where the 87 kDa protein was shown to bind prothrombin.[13] In these earlier experiments, 10 μg/ml prothrombin was used. This was unfortunate, as we have since shown that contamination with 1 ng/ml fibrinogen can detect a band of 100 ng of fibrinogen-binding protein in immunoblot experiments. When antigens were diluted to 1 or 0.1 ng per band and ligands were used at 10 ng/ml, background due to contamination in these preparations was eliminated (data not shown).

Thus the following nucleotide sequence SEQ ID NO: 7 is present in the gene coding for said protein:

```
                                            SEQ ID NO. 7
GAGCGAAGGA TACGGTCCAA GAGAAAAGAA ACCAGTGAGT

ATTAATCACA ATATCGTAGA GTACAATGAT GGTACTTTTA

AATATCAATC TAGACCAAAA TTTAACTCAA CACCTAAATA

TATTAAATTC AAACATGACT ATAATATTTT AGAATTTAAC

GATGGTACAT TCGAATATGG TGCACGTCCA CAATTTAATA

AACCAGCAGC GAAAACTGAT GCAACTATTA AAAAAGAACA

AAAATTGATT CAAGCTCAAA ATCTTGTGAG AGAATTTGAA

AAAACACATA CTGTCAGTGC ACACAGAAAA GCACAAAAGG

CAGTCAACTT AGTTTCGTTT GAATACAAAG TGAAGAAAAT

GGTCTTACAA GAGCGAATTG ATAATGTATT AAAACAAGGA

TTAGTGAG
``` whereby this nucleotide sequence SEQ ID NO: 8 encodes for the following protein starting at nucleotide 243: (In FIG. 3 nucleotides 156–242 encode a signal peptide.)

```
                                            SEQ ID NO. 8
SEGYGPREKK PVSINHNIVE YNDGTFKYQS RPKFNSTPKY

IKFKHDYNIL EFNDGTFEYG ARPQFNKPAA KTDATIKKEQ

KLIQAQNLVR EFEKTHTVSA HRKAQKAVNL VSFEYKVKKM

VLQERIDNVL KQGLVR
```

Although antisera to the 19 kDa protein recognized the 87 kDa protein (FIG. 3), pre-absorbtion with 19 kDa protein, which could eliminate the binding to the 19 kDa protein, could not completely abolish this binding to the 87 kDa protein. In addition, antisera to the 87 kDa protein did not specifically recognize the 19 kDa protein (data not shown). The immunological cross-reactivity could be due to structural similarities in the fibrinogen-binding sites of these proteins. Antisera to the 19 kDa protein also recognized the 35 kDa protein (FIG. 3). We have previously shown that the 19 kDa protein spontaneously forms 35 kDa dimers (not reducible with 2-mercapto ethanol) and to a lesser extent higher molecular weight bands that seem to be trimers and tetramers of this protein.[13] Minor bands in the preparation could thus be due to further aggregation of the 19 kDa protein or to degradation of the 87 kDa protein (FIG. 3). By pre-absorbing the rabbit anti-19 serum with either 19 or 60 kDa proteins, it was shown that there were no shared antigenic epitopes between the 60 kDa protein and 19 kDa protein (FIG. 4). it is likely that antibodies against the 60 kDa protein are present in the most normal rabbit sera. This reactivity is not due to unspecific binding to immunoglobulins. The purified 60 kDa protein did not bind control antibodies in immunoblots, and was thus shown not to contain protein A activity.

Peptide mapping analysis suggested that the 87, 60 and 19 kDa proteins are not closely related (FIG. 5). It was shown that digestion with α-chymotrypsin and staphylococcal V8 protease gave different peptide banding patterns with the three different proteins, and that the 60 kDa protein completely lost its ability to bind fibrinogen upon digestion with α-chymotrypsin, whereas the 87 and 19 kDa proteins were unaffected.

Analyses of NH$_2$-terminal sequences suggested that the 87 kDa coagulase is identical to the coagulase from strain 8325-4 (Table 1). This is in agreement with the fact that these strains produce coagulases of the same serotype. The NH$_2$-terminal sequence of the 19 kDa protein was not homologous to any of the previously described coagulases. Computer-assisted analysis revealed that this NH$_2$-terminal sequence is a new, unique sequence.[21] The strong similarity between this sequence and the NH$_2$-terminal sequence of the 35 kDa protein further strengthens the evidence that the 35 kDa protein is a dimer of the 19 kDa protein. The 60 kDa coagulase seems to represent a third type of fibrinogen-binding protein from *S. aureus*.

In the coagulase test, it was shown that highly purified preparations of both the 87 and 60 kDa proteins exerted coagulase activity (Table 2). There was a clear dose-response relationship when dilution series of the 87 and 60 kDa proteins were subjected to coagulase tests (data not shown). It appears that the 87 kDa coagulase had a higher specific activity than the 60 kDa coagulase; however, the treatment of these proteins during purification could have influenced their coagulase activities (for example the 60 kDa coagulase seemed to be more sensitive than the 87 kDa coagulase to exposure to the acetic acid used in the elution step). These clotting reactions were due to true coagulase reactivity, since no inhibition could be achieved by addition of protease inhibitors.[22,23] Addition of heparin influenced the clotting of both coagulases, such that a higher concentration of coagulase was needed for positive tests. Since heparin inhibits physiological blood clotting, we suggest that this negative effect is not due to direct interaction of heparin with staphylococcal coagulases. DFP, which is a powerful protease inhibitor, has previously been shown to inhibit both thrombin- and coagulase-mediated plasma clotting.[24] Addition of DFP to rabbit plasma inhibited clotting by both coagulases.

The amino acid sequence of a 43 kDa fragment from the *S. aureus* 213 (serotype II) coagulase has been determined.[25] The coagulase activity is contained in the NH$_2$-terminal region of this molecule, and the prothrombin-binding capacity resides further downstream within this region.[26] Coagulases from *S. aureus* BB (serotype I), *S. aureus* 213 and *S. aureus* 8325-4 (serotype III) have recently been expressed in *E. coli*.[27–29] The amino acid sequences of these recombinant coagulases reveal a quite strong homology (>90%) in the C-terminal halves of the molecules, while the NH$_2$-terminal regions show only approximately 50% homology.[30] The gene clones encoding these coagulases do not contain sequences that correspond to the NH$_2$-terminal sequence of the 19 kDa protein. The 87 kDa coagulase from strain Newman (serotype III) seems to be identical to the coagulase from *S. aureus* 8325-4. Coagulases of serotypes I and II have been shown to bind human prothrombin.[17,18]

However, it has not been established if the coagulase from strain 8325-4 binds prothrombin. It is interesting, however, that a coagulase from strain Newman, a strain of human origin, does not bind human prothrombin, although our preliminary results indicate that prothrombin is required for its function.[13] It is possible that the 60 kDa coagulase, which has a strong affinity for prothrombin and a somewhat weaker affinity for fibrinogen (as compared to the 87 kDa coagulase), has a different mode of action than the 87 kDa coagulase. The ability of the 19 kDa fibrinogen-binding protein to oligomerize, to precipitate fibrinogen in plasma and to some extent coagulate plasma, suggests that this protein could affect fibrinogen in the same manner as paracoagulating substances have been suggested to work.[19,31]

In conclusion, *S. aureus* strain Newman produces two distinct fibrinogen-binding coagulases. These are produced in a sequential manner during growth and have dif binding and antigenic properties. A third fibrinogen-binding protein is a 19 kDa protein, which spontaneously forms dimers and larger aggregates. The role of coagulases and clumping factors (or fibrinogen-binding proteins as we suggest is the correct designation for these proteins) in staphylococcal virulence and pathogenicity has not yet been established. However, in our preliminary study, 90% of 40 *S. aureus* isolates from wound infections had coagulase activity, and among these >60% produced the 87 kDa protein. It is notable that coagulases are produced in large amounts by *S. aureus* and in such a fashion that there is always one type of coagulase present in the culture medium. The fact that these proteins interact specifically with host proteins makes coagulases interesting subjects for further study. An *E. coli* clone expressing the 19 kDa protein has been isolated and sequence determination is in progress in our laboratory.

Binding of staphylococci to fibrinogen on coated coverslips or on catheters has been described (Cheung and Fischetti, 1990; Cheung et al., 1991; Herrmann et al., 1988; Kuusela et al., 1985; Mohammad et al., 1988; Vaudaux et al., 1989). It is also a well known fact that most *Staphylococcus aureus* clump in the presence of fibrinogen. It has been suggested that this clumping reaction involves a small peptide on the COOH-terminal part of the gamma chain on the fibrinogen molecule (Strong et al., 1982). On the other hand, the fibrinogen-building component of the staphylococci remained elusive for a long time. It was suggested that a fibrinogen-binding protein would be attached to the staphylococcal cell surface (Duthie, 1954; Espersen, 1987; Jeljaszewicz et al., 1983). We have identified 3 different fibrinogen-binding proteins from *Staphylococcus aureus*, all of which can be found on the staphylococcal cell surface (Bodén and Flock, 1992). However, these proteins cannot be described as cell surface proteins because they are mainly expressed extracellularly. In addition one of the identified fibrinogen-binding proteins was found to be coagulases, a well known extracellularly staphylococcal protein. The other fibrinogen-binding proteins were a second type of coagulases of 60 kDa and a 19 kDa fibrinogen-binding protein without coagulases activity. In this report we described the closing, expression and sequencing of this 19 kDa protein.

Expression of recombinant protein from the λ cloned isolated and the subclone of this was investigated (FIG. 1). The λ clone and the pBfibIII subclone both expressed a 15 kDa protein which bound fibrinogen and the anti-fib serum, whereas strain pBfibT expressed a protein of approximately 18 kDa. This was due to the fact that this construct contained a fusion product between the β-gal protein and the fib protein, lacking the first 33 amino acids. All recombinant proteins seemed to bind fibrinogen to a lesser extent than the native protein from *S. aureus*, since the binding of fibrinogen gave a weaker response that the binding of anti-fib serum in immunoblots. The opposite was true for the native protein.

The nucleotide sequence of the intact fib gene revealed an open reading frame of 165 amino acids, including a signal sequence of 29 amino acids (FIG. 3). The signal sequence had the characteristics of a typical signal sequence (Pugsley, 1989), such as a net positive charged region spanning the first 8 residues at the NH$_2$-terminus, a central core of 5 hydrophobic and 9 neutral residues with a strong probability of forming an α-helix, a turn-inducing alanine 6 residues downstream from the cleavage site, alanines at position −3 and −1 before the cleavage site and glutamic acid at position +2 in the mature protein, creating a net positive charge difference between the $NH_2$-terminus of the signal peptide and the $NH_2$-terminus of the mature polypeptide. The first 23 amino acids of the mature protein were completely homologous to the sequence obtained by $NH_2$- terminal sequence analysis of purified fib protein (Bodén and Flock, 1992). In addition, putative promote sequences and ribosomal binding site could be identified. However, there were no obvious transcription termination sequences and instead a second ribosomal binding site was identified 150 nucleotides downstream of the fib gene. This second Shine-Dalgarno sequence was followed by a start codon and a signal sequence which was homologous to the signal peptide of the fib gene. This putative peptide was no homologous to any previously described protein. One could speculate however, that these proteins are coded for by the same polycistronic transcript and thus regulated in the same way. According to our previous finding the fib protein seems to be constitutively expressed in S. aureusNewman (Bodén and Flock, 1992).

Since the previously studied protein was purified from S. aureus strain Newman the fib gene form this strain was also sequenced. Comparison between the two sequences show a remarkable resemblance (FIG. 5). The only differences being two amino acids in the signal sequence and the conservative change of the basic amino acid arginine for a likewise basic lysine at the very COOH-terminal end. On the nucleotide level there is one additional conservative nucleotide change apart for the three changes on amino acid level. Downstreams of the structural gene there are major difference between the two strains in a stretch of approximately 80 nucleotides. Closer to the putative second peptide in this transcript further downstreams the similarity is again higher, indicating that there is a similarity between the two strains also regarding this second peptide.

computer assisted analysis of the deduced amino acid sequence suggested that there was a high probability for formation of an α-helix in the signal sequence as well as in the last 60 to 70 residues of the COOH-terminus (). In addition the sequence NST at position 64-66, indicates that there is a glycosylation site. A glycosylation of the native protein could account for the discrepancy between the size of the native and the recombinant protein. When comparing the amino acid sequence of the fib protein to other known sequences in the database of the University of Wisconsin Genetics Computer Group, the protein with the highest similarity is coagulases from S. aureus. Coagulase from three different stereotypes has been cloned and sequenced (Bodén and Flock, 1992; (Kaida et al., 1989; (Kaida et al., 1987; (Phonimdaeng et al., 1990). All of these contain repeated sequences of 27 residues in the COOH-terminus. The coagulases from strain Newman has been cloned (), bu the sequence has not yet been published. A construct containing the 177 most $NH_2$-terminal amino acids of the Newman coagulases was shown to bind fibrinogen (McDevitt et al., 1992). In the fib protein a sequence of 22 amino acids, repeated twice with a spacing of 9 amino acids, located in the $NH_2$-terminal part of the mature protein showed homology to the COOH-terminal part of coagulase (FIG. 6). We suggest that this region is responsible for the fibrinogen binding.

Materials and Methods

Bacterial strains and culture conditions

Staphylococcus aureus Newman was kindly provided by M. Lindberg, Swedish University of Agriculture Sciences, Uppsala, Sweden. Staphylococci were grown overnight in Brain Heart Finfusion (BHI) medium (Difco Laboratories, Detroit, Mich.) or in Luria-Bertani (LB) medium. After centriguation, the bacterial pellet was resuspended in 20 culture volumes of freshly prepared BHI or LB and grown at 37° C. with constant shaking in Ehrlenmeyer flasks (low aeration) or in indented flasks (high aeration).

Affinity chromatography

Staphylococcal proteins were affinity purified as described previously.[10] Briefly, fibrinogen-Sepharose and prothrombin-Sepharose were prepared by coupling human fibrinogen (IMCO, Stockholm, Sweden) or human prothrombin (Sigma Chemical Co. St. Louis, Mo.) to CNBr-activated Sepharose 4B (Pharmacia, Uppsala, Sweden), by the procedure recommended by the manufacturer. The Sepharose was equilibrated with phosphate-buffered saline (PBS; 145 mM NaCl, 10 mM phosphate, pH 7.4) containing 0.05% Nonidet P-40. Staphylococcal culture supernatants supplemented with 1 mM phenylmethylsulfonyl fluoride (PMSF), 10 mM EDTA and 0.05% Nonidet P-40 were applied. The absorbed material was eluted with 0.7% acetic acid containing 0.05% Nonidet P-40. The eluted material (eluate) was concentrated in Centricon microconcentrtors (Amicon, Danvers, Mass.) or by acetone precipitation.

SDS-PAGE, affinity- and immuno-blotting

SDS-PAGE and subsequent diffusion blotting was performed using the PhastSystem (Pharmacia) as described previously.[10] Nitro-cellulose filters were incubated for 1 h at room temperature with human fibrinogen or human prothrombin at concentrations between 1 ng/ml and 10 µg/ml in PBS supplemented with 0.05% Tween 20. Primary antibodies (rabbit anti (human)fibrinogen (Dakopatts, Glostrup, Denmark), rabbit anti(human)prothrombin (Dakapatts), and rabbit anti-19 kDa protein) were diluted 1:1000 and incubated with the filters for 2 h. The rabbit anti-19 kDa protein antibodies (anti-19 serum) were obtained by subcutaneous immunization of rabbits with a highly purified 19 kDa protein preparation emulsified in complete Freund's adjuvant. In order to eliminate naturally occurring antistaphylococcal antibodies in rabbit antifibrinogen or rabbit anti prothrombin antisera, these were pre-absorbed with staphylococcal culture supernatants from cells grown in LB for 6 h. Undiluted antisera was added to 10 volumes of culture supernatant and incubated at room temperature for 1 h or at 4° C. for 4 h before diluting the antibody to the appropriate concentration. The anti-19 serum as absorbed with 19 or 60 kDa proteins purified from preparative gels. The gel slices were homogenised in PBS containing 0.1% Nonidet P-40 before being added in a 10-fold excess to the antisera and incubated as described above. Alkaline phosphatase (ALP) conjugated goat anti-rabbit immunoglobulin G antibodies (Sigma) were diluted 1:1000 and incubated with the filters for 1 h. The ALP reaction was developed in 100 mM Tris hydrochloride (pH 8.0) containing 10 mM $MgCl_2$, 0.02 mg α-naphtylphosphate per ml (E. Merck AG, Darmstadt, Germany) and 0.02 mg Fast Blue (Merck) per ml for 10–20 min.

Purification of proteins

The 87, 60 and 19 kDa protein were purified form preparative SDS-PAGE gels by eluting proteins form gel slices in a Model 422 Electro-Eluter (Bio-Rad, Hercules, Calif.).

Fragmentation of proteins by protease

Proteins were digested with 40 µg/ml of α-chymotrypsin or staphylococcal V8 protease (Sigma) for 1 h on ice.

Coagulase test

Coagulase tests were performed in Difco Coagulase Plasma (Difco) with or without the presence of the protease inhibitors N-ethylmaleimide (NEM; 2 mM), EDTA (6 mM), aprotinin (Sigma; 200 U/ml) (14), heparin (Sigma; 40 U/ml) (15), and PMSF (1 mM. Coagulate tests were also performed in the presence of 5 mM diisopropyl fluorophosphate (DFP; Janssen Chimica, Beerse, Belgium) (16).

Determination of $NH_2$-terminal sequences

Samples were analysed in a 470 Protein Sequencer (Applied Bio-systems, Foster City, Calif.).

Bacterial strains and cloning vectors

*Escherichia coli* strain Y1090 (Clontech, Palo Alto, Calif.) was used to for the screening of the λgt-11 library (Clontech) containing generic DNA from *Staphylococcus aureus* strain FDA 486. For subcloning *E. coli* strains XL-1 and JM103 were used with the cloning vectors Bluescript SK+ (Stratagene, La Jolla, Calif.), pGEM7Zf(+) (Promega) and M13mp18 or M13mp19 (Promega).

Media and chemicals

*E. coli* were grown in Luria Bertani medium at 37° C. Ampicillin (50 µg/ml) and tetracyclin (5 mg/ml) were added when appropriate. Restriction enzymes were purchased from Promega. IPTG and X-gal were from Boehringer-Mannheim. All other chemicals were purchased from Sigma (Sigma Chemical Co, St. Louis, Mo.) or Merck (E. Merck AG, Darmstadt, Germany).

Affinity chromatography

Staphylococcal proteins were affinity purified as described previously (Bodén and Flock, 1989). Breifly, fibrinogen-Sepharose was prepared by coupling human fibrinogen (IMCO, Stockholm, Sweden) to CNBr-activated Sepharose 4B (Pharmacia, Uppsala, Sweden), by the procedure recommended by the manufacturer. The Sepharose was equilibrated with phosphate-buffered saline (PBS; 145 mM NaCl, 10 mM phosphate, pH 7.4) containing 0.05% Nonidet P-40. Staphylococcal culture supernatants supplemented with 1 mM phenylmethylsulfonyl fluoride (PMSF), 10 mM EDTA and 0.05% Nonidet P-40 were applied. The absorbed material was eluted with 0.7% acetic acid containing 0.05% Nonidet P-40 . The eluted material was concentrated by acetone precipitation.

Sodium dodecyl sulphate polyacrylamide gel electrophoresis (SDS-PAGE), affinity- and immuno-blotting SDS-PAGE and subsequent diffusion blotting was performed using the phast System (Pharmacia) as described previously (Bodén and Flock, 1989). Nitrocellulose filters were incubated for 1 hour at room temperature with human fibrinogen at 10 µg/ml in PBS supplemented with 0.05% Tween 20. Primary antibodies (rabbit anti(human)fibrinogen [Dakopatts, Glostrup, Denmark] and rabbit anti-fib protein) were diluted 1:500 or 1:1000 and incubated with the filters for 2 hours. The rabbit anti-fib protein antibodies (anti-fib serum) were obtained by subcutaneous immunization of rabbits with a highly purified 19-kDa protein preparation emulsified in complete Freund's adjuvant. Alkaline phosphatase (ALP) conjugated goat anti-rabbit immunoglobulin G antibodies (Sigma) were diluted 1:1000 and incubated with the filters for 1 hour. The ALP reaction was developed in 100 mM Tris hydrochloride (pH 8.0) containing 10 mM $MgCl_2$, 0.02 mg α-naphtylphosphate per ml (E. Merck AG, DArmstadt, Germany) and 0.02 mg Fast Blue (Merck) per ml for 10–20 min.

Screening of the Agt-11 library

Plates were grown and induction with IPTG was performed according to the protocol recommended by the manufacturer (Clontech). Nitrocellulose filters (Schleicher and Schüll) were incubated with anti-fib sera diluted 1:500, as described above.

DNA sequencing and sequence analysis

The DNA sequence was determined by the dideoxy-chain termination method (Sanger et al 1977), using $[\alpha-^{35}S]dATP$ (Amersham Corp.) and Sequenase 2.0 (United States Biochemical Corporation (USB), Cleveland, Ohio). Recombinant M13mp18 or M13mp19 phage was used as template. M13 Universal primer (USB) as well as custom made primers from the Unit for. Nucleotide Synthesis, CBT, Novum (Huddinge, Sweden) were used as sequencing primers. The sequencing reaction products were resolved on 8% poly-acrylamide-urea gels. Gels were run at 40 W for 1–3 h on a Sequencing Unit from Cambridge Electrophoresis Ltd (Cambridge, England), fixed in 10% methanol, 10% acetic acid for 15 min and dried on Whatman 3MM papers under vacuum. DNA bands were visualized by autoradiography. DNA fragments containing the fib gene from strain FDA 486 and strain Newman were produced by the polymerase chain reaction (PCR) using a Perkin Elmer Cetus DNA Thermal Cycler (Perkin Elmer, Norwalk, Conn.) and Taq polymerase (Boehringer-Mannheim). The PCR generated DNA fragments were sequenced in an Applied Biosystems 373A DNA Sequencer (Applied Biosystems Inc., Foster City, Calif.) using fluorescent nucleotide terminators (). Computer assisted analysis of DNA sequences was performed with GCG software package (Genetics Computer Group 1991) and with Seq Ed software (ref).

Competition in fibrinogen binding

The three different fibrinogen binding proteins from *S. aureus* 19, 60 and 87 kD are identified. We show that each of the FgBPs, separately or together with an additive effect can block *S. aureus* binding to immobilized fibrinogen in vitro. In short, the experimental procedure was as follows: Microtiter plates were coated with fibrinogen free of contaminating plasma components (IMCO). After-coating to block non specific adherence was done with BSA. Radiolabelled bacteria were added, $2-5 \times 10^6$ per well. Simultaneously, various amounts of 19, 60 and/or 87 kD FgBP were added. Bacterial adherence was measured after two hours incubation.

Incidence of FgBPs

The incidence of the 19 and the 87 kD FgBPs were measured. Thirty nine *S. aureus* isolates of human origin and thirty seven bovine mastitis isolates, taken from a wide variety of sources, were tested by PCR for the gene and in affinity blotting for the proteins.

All (100%) of the human isolates were positive in both PCR and affinity blotting for the 19 kD protein and 95% were positive for the 87 kD (only tested by affinity blotting).

Of the bovine isolates, 45% were positive in affinity blot for the 19 kD but 95% in PCR (some variation in the genome size was found). Fifty five were positive for the 87 kD FgBP.

Vaccination

The 19 and 87 kD proteins in combination were used to immunized mice which were subsequently subjected to experimental mastitis caused by *S. aureus*. A control group was given only the adjuvant (Freund's). Histopathological examination and bacterial count was performed after 24 hours. A significant ($p<0.05$) difference in the number of colonizing bacteria was found between the two groups.

The present fibrinogen binding proteins can be used in immunization, whereby the proteins, preferably in combination with a fusion protein in order to form a larger antigen to react upon, are injected in doses creating an immunological reaction in the host mammal. Thus the fibrinogen binding proteins can be used in vaccination of mammals to protect against infections caused by staphylococcal infections.

Further, the fibrinogen binding proteins can be used to block an infection in an open skin lesion. Wounds can be treated by using a suspension comprising the fibrinogen binding protein. Thus the fibrinogen binding proteins can be used to treat wounds, e.g., for blocking bacterial binding sites in fibrinogen, or for immunization (vaccination). In the latter case the host produces specific antibodies which can protext against attachment by bacterial strains comprising such fibrinogen binding proteins. Hereby the antibodies block the adherence of the bacterial strains to damaged tissue.

Examples of colonizing of tissue damage are:
a) colonizing of wounds in skin and connective tissue, which wounds have been caused by a mechanical trauma, chemical damage, and/or thermical damage;
b) colonizing of wounds on mucous membranes such as in the mouth cavity, or in the mammary glands, urethra or vagina;
c) colonizing of connective tissue proteins, which have been exposed by minimal tissue damage (micro lesions) in connection with epithelium and endothelium (mastitis, heart valve infection, hip exchange surgery).

When using the present fibrinogen binding proteins, prepared by isolation from living cells, by means of hydrid-DNA technique, or sythesized, for immunization (vaccination) in mammals, including humans, the proteins, or polypeptides thereof, are dispersed in sterile isotonic saline solution, optionally while adding a pharmaceutically acceptable dispersing agent. Different types of adjuvants can further be used in order to sustain the release in the tissue, and thus expose the protein for a longer period of time to the immuno defence system of a body.

A suitable dose to obtain immunization is 0.5 to 5/μg of fibrinogen binding protein per kg body weight and injection at immunization. In order to obtain durable immunization, vaccinations should be carried out at consecutive occasions with an interval of 1 to 3 weeks, preferably at three occasions. Adjuvants are normally not added when repeating the immunization treatment.

When using the present fibrinogen binding proteins or polypeptides thereof for local topical administration the protein is dispersed in an isotonic saline solution to a concentration of 25 to 250/μg per ml. The wounds are then treated with such an amount only to obtain a complete wetting of the wound surface. For an average wound thus only a couple of milliliters of solution are used in this way. After treatment using the protein solution the wounds are suitably washed with isotonic saline solution or another suitable wound treatment solution.

Further the fibrinogen binding protein, or synthesized polypeptide thereof can be used to diagnose bacterial infections caused by *Staphylococcus aureus* strains, whereby a fibrinogen binding protein of the present invention is immobilized on a solid carrier, such as small latex or Sepharose$^R$ beads, whereupon sera containing antibodies are allowed to pass and react with the fibrinogen binding protein thus immobilized. The agglutination is then measured by known methods.

Further the fibrinogen binding protein or polypeptide can be used in an ELISA test (Enzyme Linked Immuno Sorbent Assay; E Engvall, Med. Biol. 55, 193 (1997)). Hereby wells in a polystyrene microtitre plate are coated with the fibrinogen binding protein and incubated over night at 4° C. The plates are then thoroughly washed using PBS containing 0.05% Tween 20, and dried. Serial dilutions of the patient serum made in PBS-Tween, are added to the wells, and are incubated at 30° C. for 1.5 hrs. After rinsing anti-human IgG conjugated with an enzyme, or a horseradish peroxidase, or an alkaline phosphatase is added to the wells and further incubated at 30° C. for 1.5 hrs. During these incubations IgG from patient serum, and added anti-human IgG-enzyme conjugate, respectively, has been bound thereto. After rinsing, an enzyme substrate is added, p-nitrophosphate in case of an alkaline phosphatase, or orthophenylene diamine substrate (OPD) in case a peroxidase has been used, respectively. The wells of the plates are then rinsed using a citrate buffer containing 0.055% OPD, and 0.005% $H_2O_2$, and incubated at 30° C. for 10 min. The enzyme reaction is stopped by adding a 4N solution of $H_2SO_4$ to each well. The colour development is measured using a spectrophotometer.

Depending on the type of enzyme substrate used a fluorescence measurement can be used as well.

Another method to diagnose *S. aureus* infections is by using the DNA gene probe method based on the nucleotide sequence for the fibrinogen binding protein or part thereof. Thereby the natural or synthetic DNA sequence is attached to a solid carrier, such as a nitrocellulose filter, a nylon filter, or a polystyrene plate as mentioned above, by e.g., adding a body fluid, to the surface. The DNA gene probe, optionally labelled enzymtically, or by a radioactive isotope, is then added to the solid surface plate comprising the DNA sequence, whereby the DNA gene probe attaches to the membrane associated sequence where appearing. The enzyme or radioactive isotope can readily be determined by known methods.

Above the term fibrinogen binding protein includes any of polypeptide thereof as well, which constitute the minimal fibrinogen binding site of the complete protein.

The fibrinogen biding protein/s can be used for raising antibodies by administering the protein and then isolating said antibodies, whereupon these are administered for passive immunization purposes.

REFERENCES

1. Duthie E S. Evidence for two forms of staphylococcal coagulase, J Gen Microbiol 1954;10:427–36.
2. Gorrill R H, Klyhn K M, McNeil E M. The initiation of infection in the mouse kidney after intravenous injection of bacteria. J Path Bacteriol 1966;91:157–72.
3. Johanovsky J. The significance of the clumping factor for pathogenicity of staphylococci. Folia Biol (Prague) 1957;3:338–42.
4. Kapral F A. Factors involved in experimental staphylococcal peritonitis. Ann NY Acad Sci 1965;128:259–73.
5. Proctor R A, Christman G, Mosher D F. Fibronectin-induced agglutination of *Staphylococcus aureus* correlates with invasiveness. J Lab Clin Med 1984; 104:455–69.
6. Espersen F, Clemmensen I. Clumping of *Staphylococcus aureus* by human fibronectin. Acta Pathol Microbiol Scand [B] 1981;89:317–21.
7. Espersen F, Schiotz P O. Normally-occurring precipitating antibodies against *Staphylococcus aureus* in human serum and colostrum. Acta Pathol Microbiol Stand [C] 1981;89:93–8.
8. Ljung Å, Hjertén S, Wadström T. High surface hydrophobicity of autoaggregating *Staphylococcus aureus* strains isolated from human infections studied with the salt aggregation test. Infect Immun 1985; 47:522–6.
9. Jeljaszewicz J, Switalski L M, Adlam C. Staphylo-coagulase and clumping factor. In: Easmon C S F, Adlam C, eds. Staphylococci and staphylococcal infections, vol. 2. London: Academic Press, 1983;525–57.
10. Cheung A L, Krishnan M, Jaffe E A, Fischetti V A. Fibrinogen acts as a bridging molecule in the adherence of *Staphylococcus aureus* to cultured human endothelial cells. J Clin Invest 1991;87:2236–45.
11. Cheung A L, Fischetti V A. The role of fibrinogen in staphylococcal adherence to catheters in vitro. J Infect Dis 1990;161:1177–86.

12. Vaudaux P, Pittet D, Haeberli A et al. Host factors selectively increase staphylococcal adherence on inserted catheters: a role for fibronectin and fibrinogen or fibrin. J Infect Dis 1989;160:865–75.
13. Bodén M K, Flock J-I. Fibrinogen-binding protein/clumping factor from *Staphylococcus aureus*. Infect Immun 1989;57:2358–63.
14. Jacherts D. Experimentelle Untersuchungen über die Identität freier und gebundener coagulase. Hyg Infektionskr 1956;142:502–9.
15. Ushioda H, Terayama T, Sakai S, Zen-Yoji H, Nishiwaki M, Hidano A. Coagulase typing of *Staphylococcus aureus* and its application in routine work. In: Jeljaszewicz J, ed. Staphylococci and staphylococcal infections, Suppl. 10. Gustav Fischer Verlag, Stuttgart, Federal Republic of Germany, 1981;77–83.
16. Reeves M W, Drummond M C, Tager M. Partial purification and characterization of the multiple molecular forms of staphylococcal clotting activity (coagulase). J Bacteriol 1981;148:861–8.
17. Kawabata S, Morita T, Iwanaga S, Igarashi H. Enzymatic properties of staphylothrombin, and active molecular complex formed between staphylocoagulase and human prothrombin. J Biochem 1985;98:1603–14.
18. Hendrix H, Lindhout T, Mertens K, Engels W, Hemker H C. Activation of human prothrombin by stoichiometric levels of staphylocoagulase. J Biol Chem 1983;258:3637–44.
19. Okano K, Saito Y, Matsushima A, Inada Y. Protamine interacts with the D-domains of fibrinogen. Biochim Biophys Acta 1981;671:164–7.
20. Peng H-L, Novick R P, Kreiswirth B, Kornblum J, Schlievert P. Cloning, characterization, and sequencing of an accessory gene regulator (agr) in *Staphylococcus aureus*. J Bacteriol 1988;170:4365–72.
21. Devereux, Haeberli, Smithies. A comprehensive set of sequence analysis programs for the VAX. Nucleic Acids Res 1984;12:387–95.
22. Heczko P B, Wegrzynowicz A, Bulanda M, Jeljaszewicz J, Pulverer G. Taxonomic implications of the pseudocoagulase activity of staphylococci. In: Jeljaszewicz J, ed. Staphylococci and staphylococcal infections, Suppl. 10. Gustav Fischer Verlag, Stuttgart, Federal Republic of Germany, 1981;43–7.
23. Wegrzynowicz Z, Heczko P B, Jeljaszewicz J, Neugebauer M, Pulverer G. Pseudocoagulase activity of staphylococci. J Clin Microbiol 1979;9:15–19.
24. Drummond M C, Tager M. Enzymatic activities associated with clotting of fibrinogen by staphylocoagulase and coagulase-reacting factor and their inhibition by diisopropylfluorophosphate. J Bacteriol 1962;83:975–80.
25. Kawabata S, Miyata T, Morita T, Miyata T, Iwanaga S, Igarashi H. The amino acid sequence of the procoagulant- and prothrombin-binding domain isolated from staphylocoagulase. J Biol Chem 1986;261:527–31.
26. Kawabata S, Morita T, Miyata t, Iwanaga S, Igarashi H. Isolation and characterization of staphylocoagulase chymotryptic fragment. J Biol Chem 1986;261:1427–33.
27. Kaida S, Miyata T, Yoshizawa Y et al. Nucleotide sequence of the staphylocoagulase gene: its unique COOH-terminal 8 tandem repeats. J Biochem 1987;102: 1117–86.
28. Kaida S, Miyata T, Yoshizawa Y, Igarashi H, Iwanaga S. Nucleotide and deduced amino acid sequences of staphylocoagulase gene from *Staphylococcus aureus* strain 213. Nucleic Acids Res 1989;17:8871.
29. Phonimdaeng P, O'Reilly M, O'Toole P W, Foster T J. Molecular cloning and expression of the coagulase gene of *Staphylococcus aureus* 8325–4. J Gen Microbiol 1988;134:75–83.
30. Phonimdaeng P, O'Reilly M, Nowlan P, Bramley A J, Foster T J. The coagulase of *Staphylococcus aureus* 8325-4. Sequence analysis and virulence of site-specific coagulase-deficient mutants. Mol Microbiol 1990;4:393–404.
31. Carr M E, Gabriel D A, Herion J C, Roberts H R. Granulocyte lysosomal cationic proteins alters fibrin assembly: a possible mechanism for granulocyte control of clot structure. J Lab Clin Med 1986;107:199–203.
32. Bodén M K, Flock J-I. (1992). Evidence for three different fibrinogen-binding protein with unique properties from *Staphylococcus aureus* strain Newman. Microbial Pathogen. 12(4):289–298.
33. Duthie E S. (1954). Evidence for two forms of staphylococcal coagulase. J Gen Microbiol. 10:427–436.
34. Espersen F. (1987). Interactions between human plasma proteins and cell wall components of *Staphylococcus aureus* Dan Med Bull. 34(2):59–69.
35. Hawiger J, Kloczewiak M, Timmons S. (1983). Interaction of fibrinogen with staphylococcal clumping factor and with platelets. Ann N Y Acad Sci. 408:521–535.
36. Hermann M, Jaconi M E, Dahlgren C, Waldvogel F A, Stendahl O, Lew D P. (1990). Neutrophil bactericidal activity against *Staphylococcus aureus* adherent on biological surfaces. Surface-bound extracellular matrix proteins activate intracellular killing by oxygen-dependent and -independent mechanisms. J Clin Invest. 86(3):942–51.
37. Herrmann M, Vaudaux P E, Pittet D, Auckenthaler R, Lew P D, Schumacher P F, Peters G, Waldvogel F A. (1988). Fibronectin, fibrinogen, and laminin act as mediators of adherence of clinical staphylococcal isolates to foreign material. J Infect Dis. 158(4):693–701.
38. Hook M, McGavin M J, Switalski L M, Raja R, Raucci G, Lindgren P E, Lindberg M, Signas C. (1990). Interactions of bacteria with extracellular matrix proteins. Cell Differ Dev. 32(3):433–8.
39. Kuusela P. (1978). Fibronectin binds to *Staphylococcus aureus* Nature (London). 276:718–720.
40. Kuusela P, Vartio T, Vuento M, Myhre E B. (1985). Attachment of staphylococci and streptococci on fibronectin, fibronectin fragments, and fibrinogen bound to a solid phase. Infect Immun. 50(1):77–81.
41. McDevitt D, Vaudaux P, Foster T J. (1992). Genetic evidence that bound coagulase of *Staphylococcus aureus* is not clumping factor. Infect Immun. 60(4):1514–23.
42. Mohammad S F, Topham N S, Burns G L, Olsen D B. (1988). Enhanced bacterial adhesion on surfaces pretreated with fibrinogen and fibronectin. Asaio Trans. 34(3):573–7.
43. Muller E, Takeda S, Goldmann D A, Pier G B. (1991). Blood proteins do not promote adherence of coagulase-negative staphylococci to biomaterials. Infect Immun. 59(9):3323–6.
44. Phonimdaeng P, O'Reilly M, Nowlan P, Bramley A J, Foster T J. (1990). The coagulase of *Staphylococcus aureus* 8325-4. Sequence analysis and virulence of site-specific coagulase-deficient mutants. Mol Microbiol. 4(3):393–404.
45. Pugsley A P. (1989). Early stages in the secretory pathway. In Protein targeting. (ed.). San Diego: Academic Press, Inc., pp. 46–48.
46. Raus J, Love D N. (1991). Comparison of the affinities to bovine and human prothrombin of the staphylocoagulases from *Staphylococcus intermedius* and *Staphylococcus aureus* of animal origin. J Clin Microbiol. 29(3):570–2.

47. Strong D D, Laudano A L, Hawiger J, Doolittle R F. (1982). Isolation, characterization, and synthesis of peptides from human fibrinogen that block the staphylococcal clumping reaction and construction of a synthetic clumping particle. Biochemistry. 21:1414–1420.
48. Vaudaux P, Pittet D, Haeberli A, Huggler E, Nydegger U E, Lew D P, Waldvogel F A. (1989). Host factors selectively increase staphylococcal adherence on inserted catheters: a role for fibronectin and fibrinogen or fibrin. J Infect Dis. 160(5):865–75.

BRIEF DESCRIPTION OF FIGURES

FIG. 3. SEQ ID NO:9 Nucleotide and amino acid sequence for the fib protein gene. The box denotes a possible Shine-Dalgarno sequence. Putative promoter sequences are underlined. The vertical arrow indicates the cleavage site of the signal sequence.

FIG. 4. SEQ ID NO:10–11 Comparison of the nucleotide sequences for the fib gene from strain FDA 486 (top sequence) and strain Newman. Similarity is shown by blank spaces, differences in sequence is indicated by the diverging nucleotide of the Newman fib gene.

FIG. 5. SEQ ID NO:12–13 Comparison of the amino acid sequences for the fib protein from strain FDA 486 (top sequence) and strain Newman. Similarity is shown by blank spaces, differences in sequence is indicated by the diverging amino acid of the Newman protein.

FIG. 6. SEQ ID NO:14–15 Sequence homologies between the fib protein and the coagulase from S. aureus. Bold letter show homologies between the two repeats in the fib protein. Shaded letters show homologies between the fib protein and coagulase.

Figure 1:
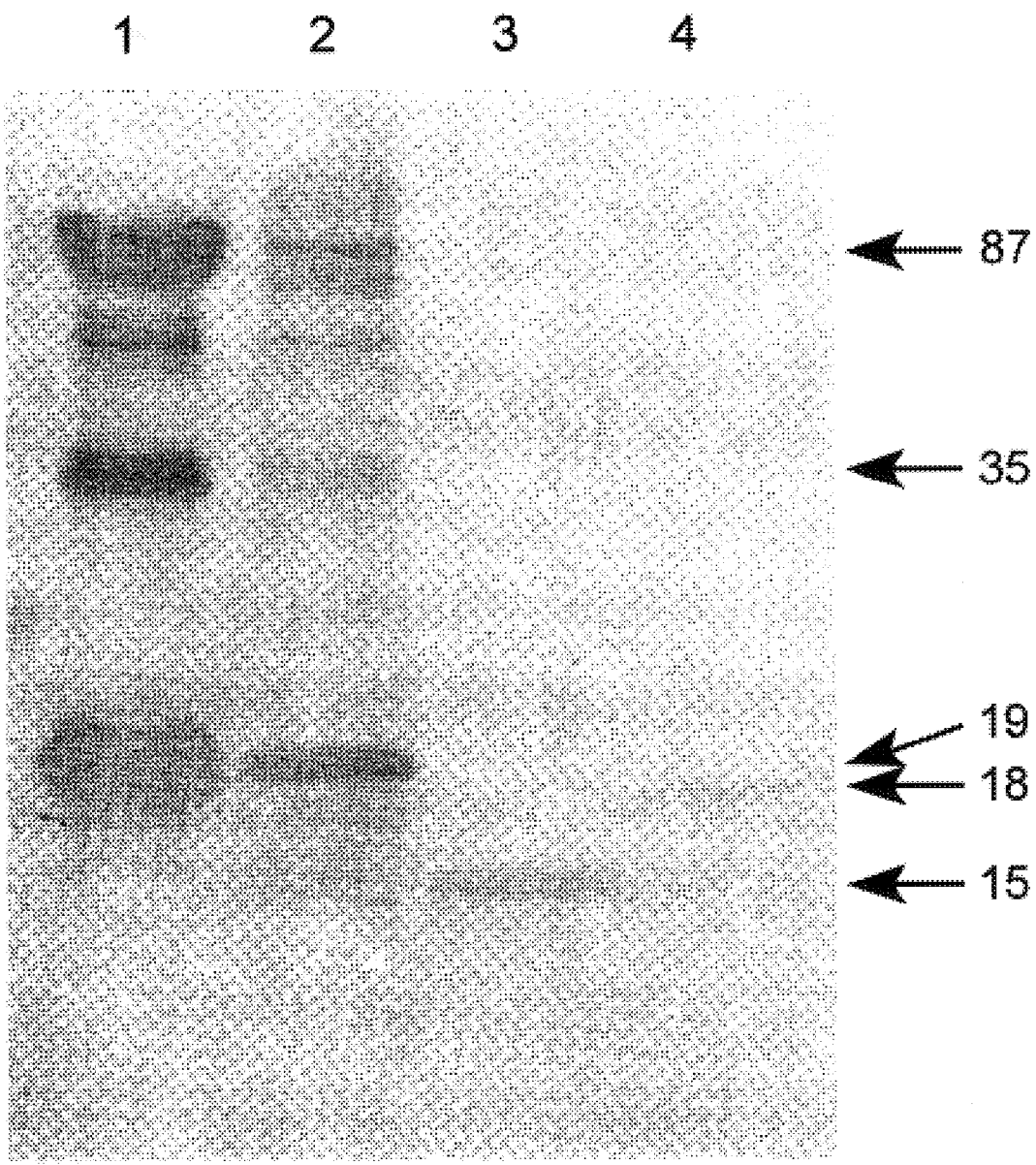
FIG. 1. Analysis of affinity purified material from fibrinogen-Sepharose. Arrows indicate molecular masses (in kDa). Immunoblot probed with anti-19 serum. Lanes: 1, fibrinogen-proteins from S. aureus strain Newman; 2, fibrinogen-proteins from S. aureus strain FDA 486; 3, fibrinogen-proteins from E. coli XL-1 harbouring plasmid pBfibIII; 4, fibrinogen-proteins from E. coli XL-1 harbouring plasmid pBfibT.

What is claimed is:

1. A method for immunization, wherein a protein or fragment thereof is administered to a mammal in an amount sufficient to raise antibodies to that protein, wherein said protein or fragment thereof comprises the amino acid sequence set forth in SEQ ID NO:8, or a fragment thereof retaining that portion of the sequence responsible for fibrinogen binding activity.

2. A method for immunization, whereby an antibody raised in accordance with claim 1 is administered to a mammal in an amount sufficient to provide a passive immunization.

3. A method for immunizing a mammal against Staphylococcus infection according to claim 1, comprising administering to said mammal a fibrinogen binding protein derived from Staphylococci or fragment thereof retaining fibrinogen binding activity, in an amount sufficient to raise antibodies to the protein, wherein said protein has a molecular weight of 19 kDa.

4. A method for immunizing a mammal against Staphylococcus infection according to claim 1, comprising administering to said mammal an antibody to a fibrinogen binding protein or fragment thereof retaining fibrinogen binding activity in an amount sufficient to provide a passive immunization, wherein said protein has a molecular weight of 19 kDa.

* * * * *

UNITED STATES PATENT AND TRADEMARK OFFICE
CERTIFICATE OF CORRECTION

Figure 2:
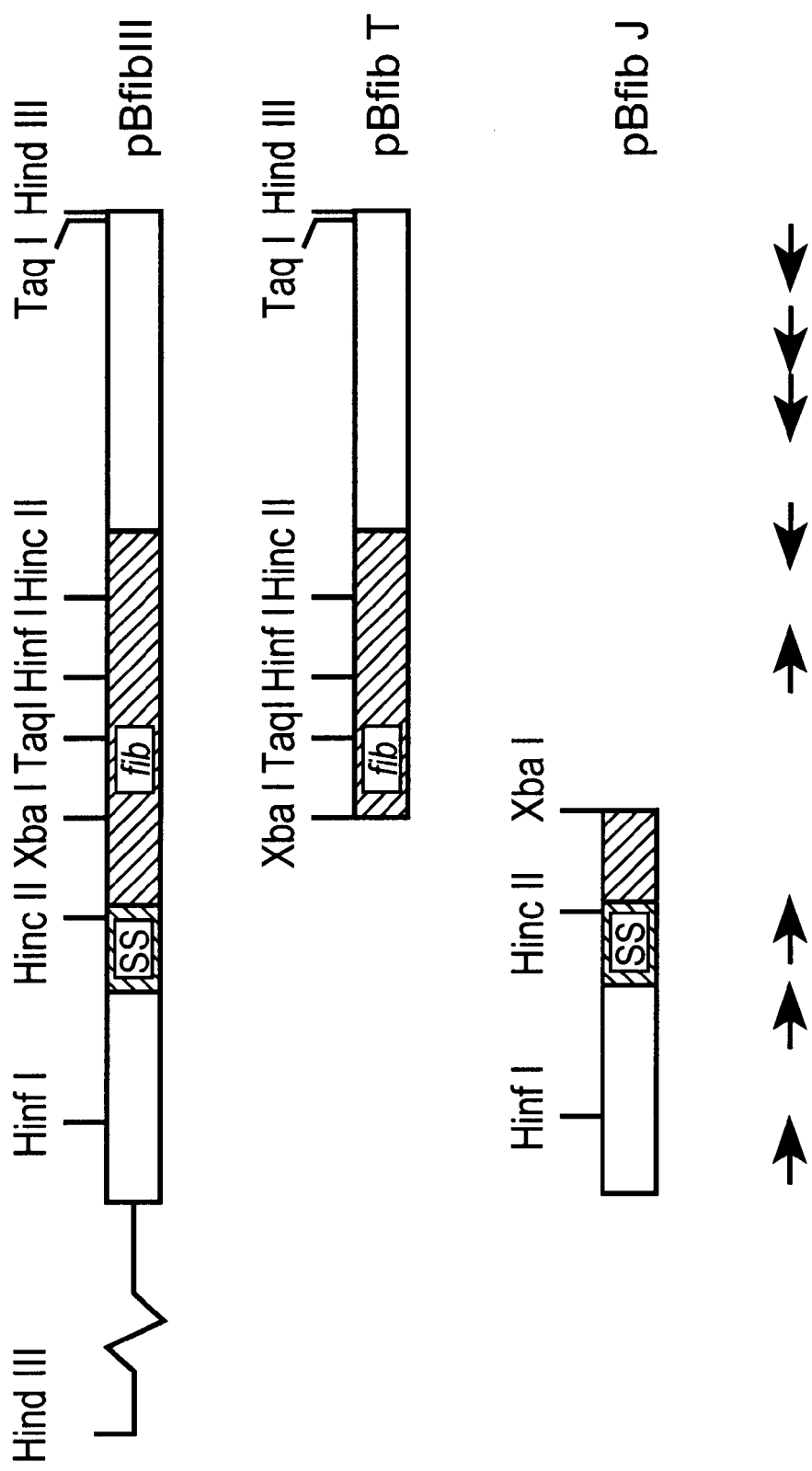
FIG. 2. Restriction map and sequencing strategy of the insert containing the fib gene. Subcloning of the fib gene from the original λ clone on a HindIII—HindIII fragment resulted in the pBfibIII vector. This was further subcloned into the pBfibT and pBfib J vectors. Boxes show the regions for which the sequence was deduced. SS denotes the signal sequence and fib the structural gene for the mature fib protein. Arrows indicate the primers used for sequencing.
Figure 7:
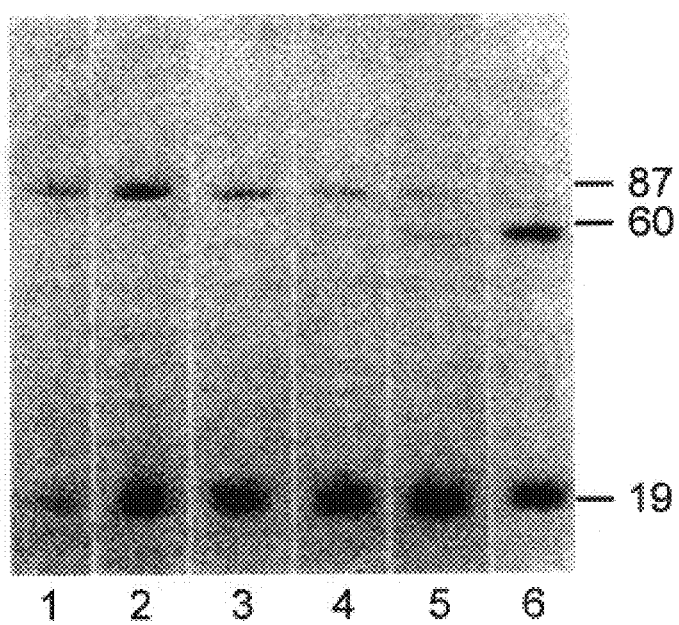
FIG. 7. Coomassie blue-stained SDS-PAGE of fibrinogen-binding material, affinity purified from S. aureus culture supernatants. Cells were grown in LB under low aeration conditions and samples were taken every hour. Lanes 1–6 represent samples taken after 1, 2, 3, 5, 7 and 9 h.
Figure 9:
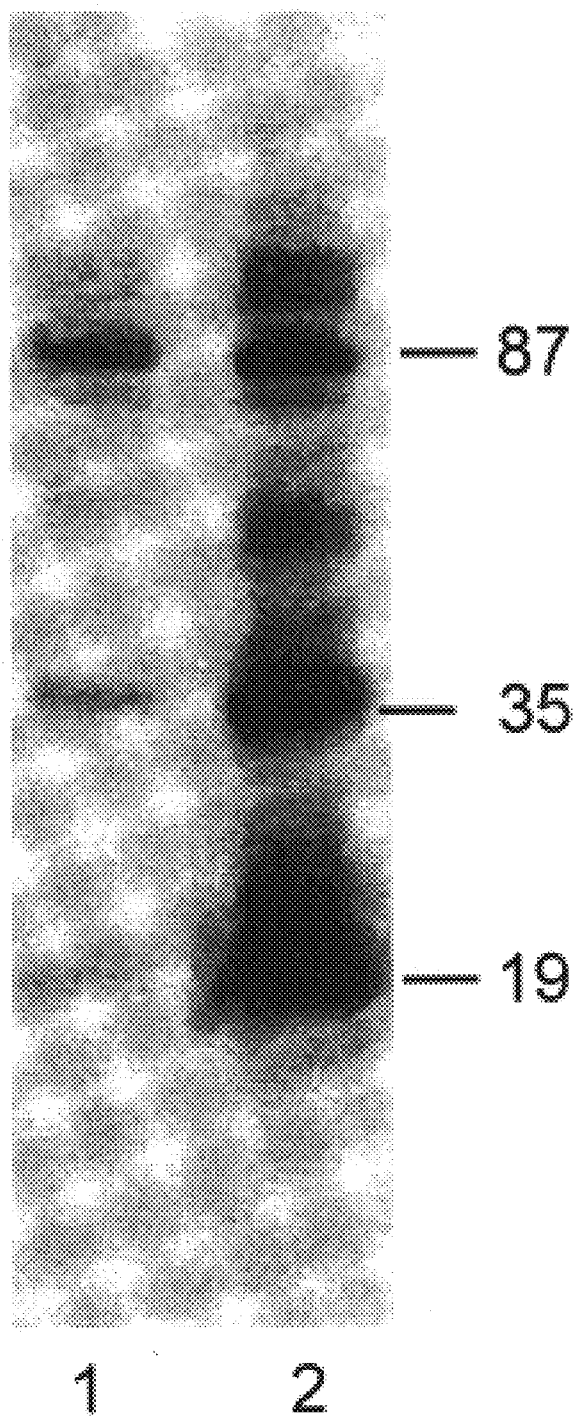
FIG. 9. Immunoblot analysis of eluate from fibrinogen-Sepharose. Lanes: 1, eluate (undiluted) incubated with fibrinogen (20 ng/ml) and antifibrinogen antibody; 2, eluate (undiluted) incubated with anti-19 serum.
Figure 10:
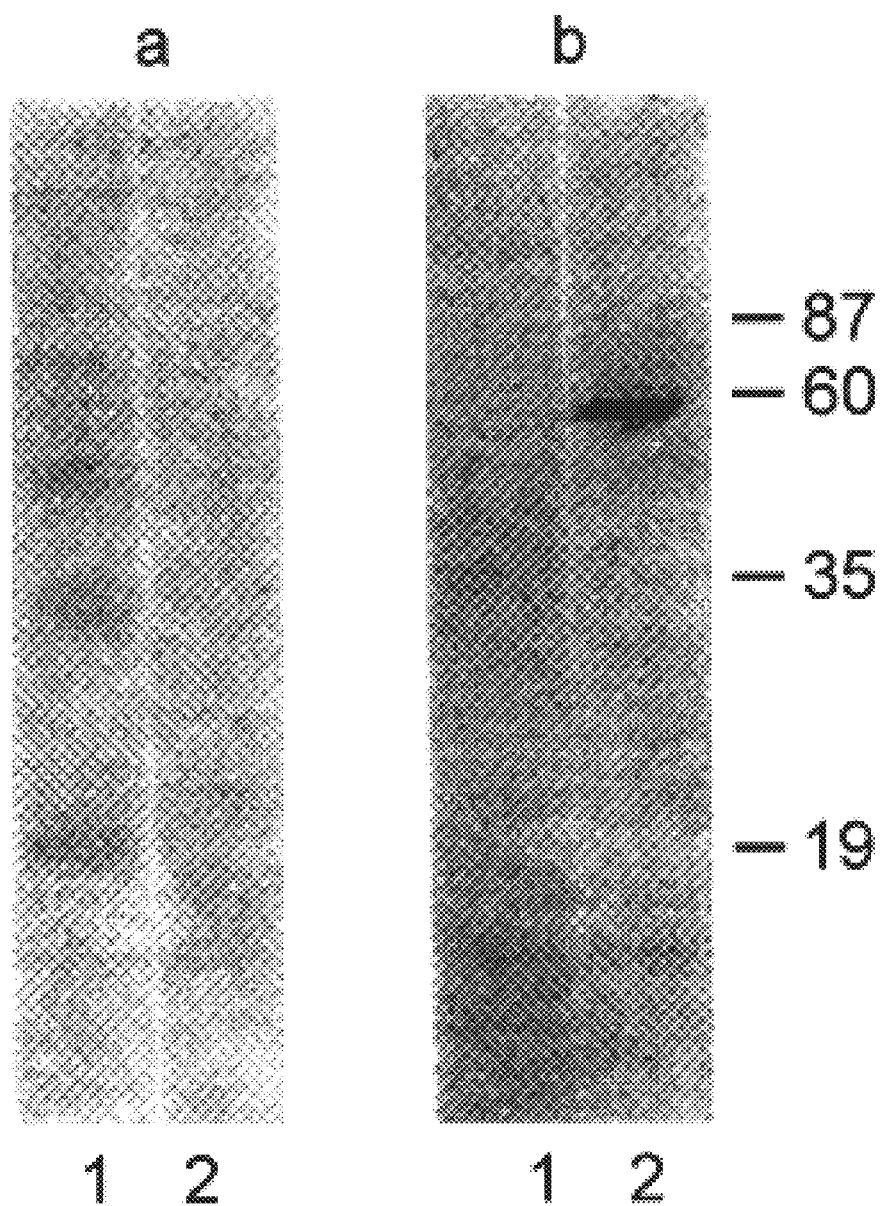
FIG. 10. Immunoblot analysis of eluate (diluted 1/100) from fibrinogen- and prothrombin-Sepharose prepared as indicated in FIG. 2 (a) Anti-19 serum pre-absorbed with the 60-kDa protein; (b) Anti-19 serum pre-absorbed with the 19-kDa protein. Lanes: 1, eluate from fibrinogen-Sepharose; 2, eluate from prothrombin-Sepharose.

PATENT NO.    : 6,299,879 B1
DATED         : October 9, 2001
INVENTOR(S)   : Maria K. Bodén Wästfält and Jan-Ingmar Flock It is certified that error appears in the above-identified patent and that said Letters Patent is hereby corrected as shown below:

Drawings,
Sheet 1, Fig. 1, should read -- Fig. 6. --;
Sheet 2, Fig. 2, should read -- Fig. 7. --;
Sheet 3, Fig. 3, should read -- Fig. 8. --;
Sheet 4, Fig. 4, should read -- Fig. 9. --;
Sheet 5, Fig. 5, should read -- Fig. 10. --;
Sheet 6, Fig. 6, should read -- Fig. 11. --;
Sheet 7, Fig. 7, should read -- Fig. 1. --;
Sheet 7, Fig. 8, should read -- Fig. 2. --;
Sheet 8, Fig. 9, should read -- Fig. 3. --;
Sheet 9, Fig. 10, should read -- Fig. 4. --; and
Sheet 10, Fig. 11, should read -- Fig. 5. --.

Column 4,
Line 33, replace "(FIG. 1.)" with -- (FIG. 6.) --;
Line 44, replace "(FIG. 2.)" with -- (FIG. 7.) --;
Line 47, replace "(FIG. 1.)" with -- (FIG. 6.) --;
Line 51, replace "(FIG. 2.)" with -- (FIG. 7.) --;
Line 54, replace "(FIG. 1.)" with -- (FIG. 6.) --; and
Line 60, replace ". . ." with -- 8513 --.

Figure 8:
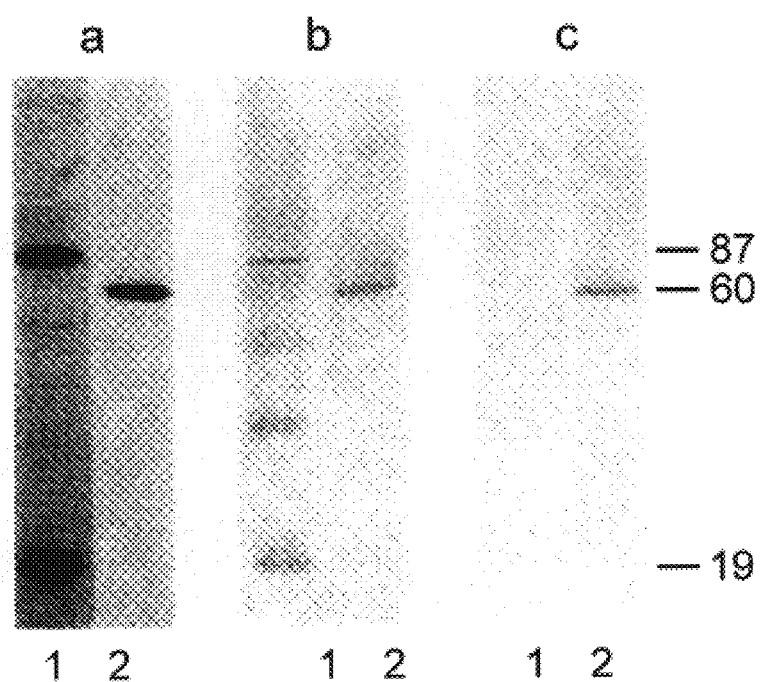
FIG. 8. Analysis of affinity purified material from fibrinogen- and prothrombin-Sepharose. (a) Coomassie blue stained, undiluted eluate; (b) Immunoblot of eluate (diluted 1/100), probed with fibrinogen (10 μg/ml) and pre-absorbed antifibrinogen antibody; (c) immunoblot of eluate (diluted 1/100), probed with prothrombin (10 μg/ml) and pre-absorbed antiprothrombin antibody. Lanes: 1, eluate from fibrinogen-Sepharose purified from culture supernatants of staphylococci grown in BHI for 3–4 h; 2, eluate from prothrombin-Sepharose purified from culture supernatants of staphylococci grown in LB for 6–8 h and initially passed through fibrinogen-Sepharose.

Column 5,
Line 9, replace "FIG. 3." with -- FIG. 8. --;
Line 12, replace "(FIG. 2)" with -- (FIG. 7) --;
Line 18, replace "FIG. 4." with -- FIG. 9. --;
Line 22, replace "FIG. 5." with -- FIG. 10. --; and
Lines 23-33, replace "(FIG. 6)" with -- (FIG. 11) --.

Column 6,
Lines 24-25, replace "(FIG. 3)" with -- (FIG. 8) --.

Column 8,
Line 47, replace "(FIG. 1)" with -- (FIG. 6) --; and
Line 60, replace "(FIG. 3)" with -- (FIG 8) --.

Column 9,
Line 24, replace "(FIG. 5)" with -- (FIG. 10) --; and
Line 60, replace ("FIG. 6)" with -- (FIG. 11) --.

UNITED STATES PATENT AND TRADEMARK OFFICE
CERTIFICATE OF CORRECTION

PATENT NO.    : 6,299,879 B1
DATED         : October 9, 2001
INVENTOR(S)   : Maria K. Bodén Wästfält and Jan-Ingmar Flock It is certified that error appears in the above-identified patent and that said Letters Patent is hereby corrected as shown below:

Column 11,
Line 59, replace "Agt-11" with -- λgt-11 --.

Column 17,
Line 13, replace "FIG. 1." with -- FIG. 6. --;
Line 21, replace "FIG. 2." with -- FIG. 7. --;
Line 30, replace "FIG. 3." with -- FIG. 8. --;
Line 35, replace "FIG. 4." with -- FIG. 9. --; and
Line 40, replace "FIG. 5." with -- FIG. 10. --.

Figure 11:
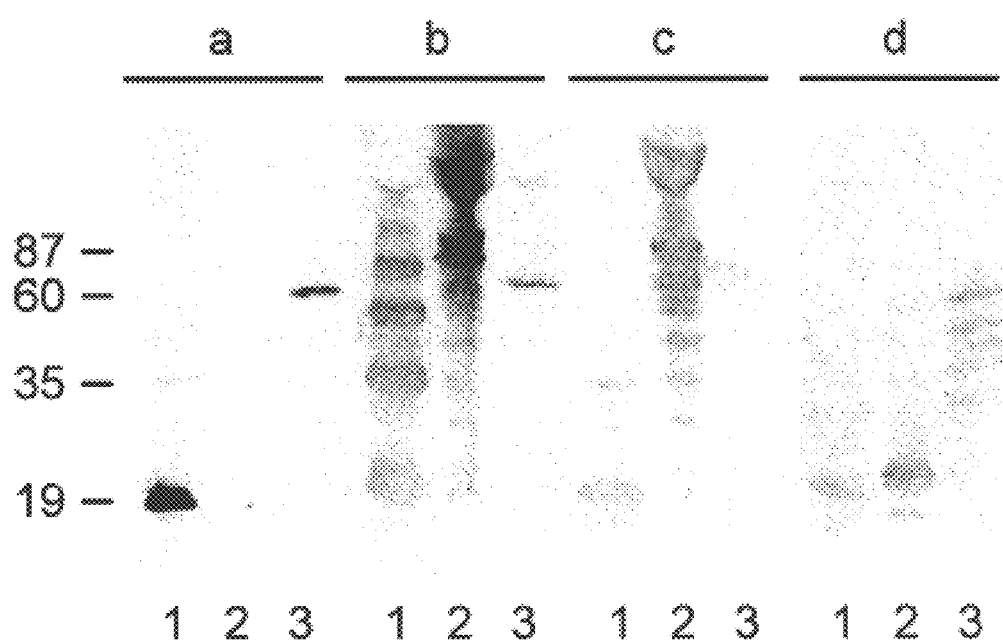
FIG. 11. Analysis of purified proteins eluted from preparative SDS-PAGE gels. (a) Silver stain of undigested sample; (b–d) immunoblots probed with fibrinogen and antifibrinogen antibodies; (b) undigested sample; (c) samples digested with α-chymotrypsin; (d) samples digested with staphylococcal V8 protease. Lanes: 1, 19 kDa protein; 2, 87 kDa protein; 3, 60 kDa protein.

Column 18,
Line 3, replace "FIG. 6." with -- FIG. 11. --;
Line 8, replace "FIG. 7." with -- FIG. 1. --;
Line 14, replace "FIG. 8." with -- FIG. 2. --;
Line 26, replace "FIG. 9." with -- FIG. 3. --;
Line 30, replace "FIG. 10." with -- FIG. 4. --; and
Line 36, replace "FIG. 11." with -- FIG. 5. --.

Column 21,
Line 11, replace "Met Tyr Pro Glu Lys Lys Pro Val" with
                               5
-- Met—Tyr ——Pro—Glu Lys Lys Pro Val --.
                 5

Signed and Sealed this

First Day of October, 2002

Attest:

JAMES E. ROGAN
*Attesting Officer*     *Director of the United States Patent and Trademark Office*

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
      (A) LENGTH: 20 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:1:

Ile Val Thr Lys Asp Tyr Ser Lys Glu Ser Arg Val Asn Glu Asn Ser
1            5                  10                15

Lys Tyr Gly Thr
        20

(2) INFORMATION FOR SEQ ID NO:2:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

Ile Val Thr Lys Asp Tyr Ser Lys Glu Ser Arg Val Asn Glu Lys Ser
1               5                   10                  15

Lys Lys Gly Ala
            20

(2) INFORMATION FOR SEQ ID NO:3:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

Ile Val Thr Lys Asp Tyr Ser Gly Lys Ser Gln Val Asn Ala Gly Ser
1               5                   10                  15

Lys Asn Gly Thr
            20

(2) INFORMATION FOR SEQ ID NO:4:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

Ile Val Thr Lys Asp Tyr Ser Gly Lys Ser Gln Val Asn Ala Gly Ser
1               5                   10                  15

Lys Asn Gly Thr
            20

(2) INFORMATION FOR SEQ ID NO:5:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

Ser Glu Gly Tyr Gly Pro Arg Glu Lys Lys Pro Val Ser Ile Asn His
1               5                   10                  15

Asn Ile Val Glu
            20

(2) INFORMATION FOR SEQ ID NO:6:

```
        (i) SEQUENCE CHARACTERISTICS:
             (A) LENGTH: 8 amino acids
             (B) TYPE: amino acid
             (C) STRANDEDNESS: single
             (D) TOPOLOGY: linear (ii) MOLECULE TYPE: protein (xi) SEQUENCE DESCRIPTION: SEQ ID NO:6:

Met Tyr Pro Glu Lys Lys Pro Val
1               5

(2) INFORMATION FOR SEQ ID NO:7:

(i) SEQUENCE CHARACTERISTICS:
             (A) LENGTH: 408 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:7:

GAGCGAAGGA TACGGTCCAA GAGAAAAGAA ACCAGTGAGT ATTAATCACA ATATCGTAGA      60

GTACAATGAT GGTACTTTTA AATATCAATC TAGACCAAAA TTTAACTCAA CACCTAAATA     120

TATTAAATTC AAACATGACT ATAATATTTT AGAATTTAAC GATGGTACAT TCGAATATGG     180

TGCACGTCCA CAATTTAATA AACCAGCAGC GAAAACTGAT GCAACTATTA AAAAGAACA      240

AAAATTGATT CAAGCTCAAA ATCTTGTGAG AGAATTTGAA AAAACACATA CTGTCAGTGC     300

ACACAGAAAA GCACAAAAGG CAGTCAACTT AGTTTCGTTT GAATACAAAG TGAAGAAAAT     360

GGTCTTACAA GAGCGAATTG ATAATGTATT AAAACAAGGA TTAGTGAG                 408

(2) INFORMATION FOR SEQ ID NO:8:

(i) SEQUENCE CHARACTERISTICS:
             (A) LENGTH: 136 amino acids
             (B) TYPE: amino acid
             (C) STRANDEDNESS: single
             (D) TOPOLOGY: linear (ii) MOLECULE TYPE: protein (xi) SEQUENCE DESCRIPTION: SEQ ID NO:8:

Ser Glu Gly Tyr Gly Pro Arg Glu Lys Lys Pro Val Ser Ile Asn His
1               5                  10                  15

Asn Ile Val Glu Tyr Asn Asp Gly Thr Phe Lys Tyr Gln Ser Arg Pro
            20                  25                  30

Lys Phe Asn Ser Thr Pro Lys Tyr Ile Lys Phe Lys His Asp Tyr Asn
        35                  40                  45

Ile Leu Glu Phe Asn Asp Gly Thr Phe Glu Tyr Gly Ala Arg Pro Gln
    50                  55                  60

Phe Asn Lys Pro Ala Ala Lys Thr Asp Ala Thr Ile Lys Lys Glu Gln
65                  70                  75                  80

Lys Leu Ile Gln Ala Gln Asn Leu Val Arg Glu Phe Glu Lys Thr His
                85                  90                  95

Thr Val Ser Ala His Arg Lys Ala Gln Lys Ala Val Asn Leu Val Ser
            100                 105                 110

Phe Glu Tyr Lys Val Lys Lys Met Val Leu Gln Glu Arg Ile Asp Asn
        115                 120                 125

Val Leu Lys Gln Gly Leu Val Arg
```

|     130         |     135         |

(2) INFORMATION FOR SEQ ID NO:9:

(i) SEQUENCE CHARACTERISTICS:
      (A) LENGTH: 1009 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 157..654

(ix) FEATURE:
      (A) NAME/KEY: CDS
      (B) LOCATION: 804..1007

(xi) SEQUENCE DESCRIPTION: SEQ ID NO:9:

```
GACTAGTGTA TAAGTGCTGA TGAGTCACAA GATAGATAAC TATATTTTGT CTATATTATA      60

AAGTGTTTAT AGTTAATTAA TAATTAGTTA ATTTCAAAAG TTGTATAAAT AGGATAACTT     120

AATAAATGTA AGATAATAAT TTGGAGGATA ATTAAC ATG AAA AAT AAA TTG ATA       174
                                       Met Lys Asn Lys Leu Ile
                                         1               5

GCA AAA TCT TTA TTA ACA ATA GCG GCA ATT GGT ATT ACT ACA ACT ACA       222
Ala Lys Ser Leu Leu Thr Ile Ala Ala Ile Gly Ile Thr Thr Thr Thr
         10                  15                  20

ATT GCG TCA ACA GCA GAT GCG AGC GAA GGA TAC GGT CCA AGA GAA AAG       270
Ile Ala Ser Thr Ala Asp Ala Ser Glu Gly Tyr Gly Pro Arg Glu Lys
             25                  30                  35

AAA CCA GTG AGT ATT AAT CAC AAT ATC GTA GAG TAC AAT GAT GGT ACT       318
Lys Pro Val Ser Ile Asn His Asn Ile Val Glu Tyr Asn Asp Gly Thr
 40                  45                  50

TTT AAA TAT CAA TCT AGA CCA AAA TTT AAC TCA ACA CCT AAA TAT ATT       366
Phe Lys Tyr Gln Ser Arg Pro Lys Phe Asn Ser Thr Pro Lys Tyr Ile
 55                  60                  65                  70

AAA TTC AAA CAT GAC TAT AAT ATT TTA GAA TTT AAC GAT GGT ACA TTC       414
Lys Phe Lys His Asp Tyr Asn Ile Leu Glu Phe Asn Asp Gly Thr Phe
                 75                  80                  85

GAA TAT GGT GCA CGT CCA CAA TTT AAT AAA CCA GCA GCG AAA ACT GAT       462
Glu Tyr Gly Ala Arg Pro Gln Phe Asn Lys Pro Ala Ala Lys Thr Asp
             90                  95                 100

GCA ACT ATT AAA AAA GAA CAA AAA TTG ATT CAA GCT CAA AAT CTT GTG       510
Ala Thr Ile Lys Lys Glu Gln Lys Leu Ile Gln Ala Gln Asn Leu Val
         105                 110                 115

AGA GAA TTT GAA AAA ACA CAT ACT GTC AGT GCA CAC AGA AAA GCA CAA       558
Arg Glu Phe Glu Lys Thr His Thr Val Ser Ala His Arg Lys Ala Gln
 120                 125                 130

AAG GCA GTC AAC TTA GTT TCG TTT GAA TAC AAA GTG AAG AAA ATG GTC       606
Lys Ala Val Asn Leu Val Ser Phe Glu Tyr Lys Val Lys Lys Met Val
135                 140                 145                 150

TTA CAA GAG CGA ATT GAT AAT GTA TTA AAA CAA GGA TTA GTG AGA TAA       654
Leu Gln Glu Arg Ile Asp Asn Val Leu Lys Gln Gly Leu Val Arg  *
                 155                 160                 165

TACTTCTGTC ATTATTTTAA GTTCAAAATA ATTTAATATT ATATTATTTT TTATTAATAA     714

AACGACTATG CTATTTAATG CCAGGTTAAT GTAACTTTCC TAAAATTGAC TATATAATCG     774

TTAAGTATCA ATTTTAAGGA GAGTTTACA ATG AAA TTT AAA AAA TAT ATA TTA       827
                               Met Lys Phe Lys Lys Tyr Ile Leu
                                 1               5
```

| | | | | | | | | | | | | | | | | |
|---|---|---|---|---|---|---|---|---|---|---|---|---|---|---|---|---|
| ACA | GGA | ACA | TTA | GCA | TTA | CTT | TTA | TCA | TCA | ACT | GGG | ATA | GCA | ACT | ATA | 875 |
| Thr | Gly | Thr | Leu | Ala | Leu | Leu | Leu | Ser | Ser | Thr | Gly | Ile | Ala | Thr | Ile | |
| | 10 | | | | 15 | | | | | 20 | | | | | | |
| GAA | GGG | AAT | AAA | GCA | GAT | GCA | AGT | AGT | CTG | GAC | AAA | TAT | TTA | ACT | GAA | 923 |
| Glu | Gly | Asn | Lys | Ala | Asp | Ala | Ser | Ser | Leu | Asp | Lys | Tyr | Leu | Thr | Glu | |
| 25 | | | | | 30 | | | | | 35 | | | | | 40 | |
| AGT | CAG | TTT | CAT | GAT | AAA | CGC | ATA | GCA | GAA | GAA | TTA | AGA | ACT | TTA | CTT | 971 |
| Ser | Gln | Phe | His | Asp | Lys | Arg | Ile | Ala | Glu | Glu | Leu | Arg | Thr | Leu | Leu | |
| | | | | 45 | | | | | 50 | | | | | 55 | | |
| AAC | AAA | TCG | AAT | GTA | TAT | GCA | TTA | GCT | GCA | GGA | AGC | TT | | | | 1009 |
| Asn | Lys | Ser | Asn | Val | Tyr | Ala | Leu | Ala | Ala | Gly | Ser | | | | | |
| | | | | 60 | | | | | 65 | | | | | | | |

(2) INFORMATION FOR SEQ ID NO:10:

(i) SEQUENCE CHARACTERISTICS:
        (A) LENGTH: 781 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

```
ATAGATAACT ATATTTTGTC TATATTATAA AGTGTTTATA GTTAATTAAT AATTAGTTAA      60

TTTCAAAAGT TGTATAAATA GGATAACTTA ATAAATGTAA GATAATAATT TGGAGGATAA     120

TTAACATGAA AAATAAATTG ATAGCAAAAT CTTTATTAAC AATAGCGGCA ATTGGTATTA     180

CTACAACTAC AATTGCGTCA ACAGCAGATG CGAGCGAAGG ATACGGTCCA AGAGAAAAGA     240

AACCAGTGAG TATTAATCAC AATATCGTAG AGTACAATGA TGGTACTTTT AAATATCAAT     300

CTAGACCAAA ATTTAACTCA ACACCTAAAT ATATTAAATT CAAACATGAC TATAATATTT     360

TAGAATTTAA CGATGGTACA TTCGAATATG GTGCACGTCC ACAATTTAAT AAACCAGCAG     420

CGAAAACTGA TGCAACTATT AAAAAGAAC AAAAATTGAT TCAAGCTCAA AATCTTGTGA     480

GAGAATTTGA AAAACACAT ACTGTCAGTG CACACAGAAA AGCACAAAAG GCAGTCAACT     540

TAGTTTCGTT TGAATACAAA GTGAAGAAAA TGGTCTTACA AGAGCGAATT GATAATGTAT     600

TAAAACAAGG ATTAGTGAGA TAATACTTCT GTCATTATTT TAAGTTCAAA ATAATTTAAT     660

ATTATATTAT TTTTTATTAA TAAAACGACT ATGCTATTTA ATGCCAGGTT AATGTAACTT     720

TCCTAAAATT GACTATATAA TCGTTAAGTA TCAATTTTAA GGAGAGTTTA CAATGAAATT     780

T                                                                    781
```

(2) INFORMATION FOR SEQ ID NO:11:

(i) SEQUENCE CHARACTERISTICS:
        (A) LENGTH: 785 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

```
ATAGATAGCT ATATTCAGTC TATATTATAA AGTGTTTATA GTTAATTAAT AATTAGTTAA      60

TTTCAAAAGT TGTATAAATA GGATAACTTA ATAAATGTAA GATAATAATT TGGAGGATAA     120

TTGACATGAA AAATGCATTG ATAGCAAAAT CTTTATTAAC ATTAGCGGCA ATAGGTATTA     180

CTACAACTAC AATTGCGTCA ACAGCAGATG CGAGCGAAGG ATACGGTCCA AGAGAAAAGA     240

AACCAGTGAG TATTAATCAC AATATCGTAG AGTACAATGA TGGTACTTTT AAATATCAAT     300
```

CTAGACCAAA ATTTAACTCA ACACCTAAAT ATATTAAATT CAAACATGAC TATAATATTT    360

TAGAATTTAA CGATGGTACA TTCGAATATG GTGCACGTCC ACAATTTAAT AAACCAGCAG    420

CGAAAACTGA TGCAACTATT AAAAAGAAC AAAAATTGAT TCAAGCTCAA AATCTTGTGA    480

GAGAATTTGA AAAACACAT ACTGTCAGTG CACACAGAAA AGCACAAAAG GCAGTCAACT    540

TAGTTTCGTT TGAATACAAA GTGAAGAAAA TGGTCTTACA AGAGCGAATT GATAATGTAT    600

TAAAACAAGG ATTAGTTAAA TAAAACTTCA ATCGTTGCTG TTATCTGGAA ATAATTAATT    660

AAATGTTATG TTAATTTTTG TTAATGAAAA AAGTAATCTA TTTAATGACA GGTTAATGTA    720

ATTGTCCTGA AATTGACTAT ATACTCAGTA AGTATCAATT TTAAGGAGAG CTTATAATGA    780

AATTT    785

(2) INFORMATION FOR SEQ ID NO:12:

(i) SEQUENCE CHARACTERISTICS:
        (A) LENGTH: 165 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:12:

Met Lys Asn Lys Leu Ile Ala Lys Ser Leu Leu Thr Ile Ala Ala Ile
1               5                   10                  15

Gly Ile Thr Thr Thr Thr Ile Ala Ser Thr Ala Asp Ala Ser Glu Gly
            20                  25                  30

Tyr Gly Pro Arg Glu Lys Lys Pro Val Ser Ile Asn His Asn Ile Val
        35                  40                  45

Glu Tyr Asn Asp Gly Thr Phe Lys Tyr Gln Ser Arg Pro Lys Phe Asn
    50                  55                  60

Ser Thr Pro Lys Tyr Ile Lys Phe Lys His Asp Tyr Asn Ile Leu Glu
65                  70                  75                  80

Phe Asn Asp Gly Thr Phe Glu Tyr Gly Ala Arg Pro Gln Phe Asn Lys
                85                  90                  95

Pro Ala Lys Thr Asp Ala Thr Ile Lys Lys Glu Gln Lys Leu Ile
            100                 105                 110

Gln Ala Gln Asn Leu Val Arg Glu Phe Glu Lys Thr His Thr Val Ser
        115                 120                 125

Ala His Arg Lys Ala Gln Lys Ala Val Asn Leu Val Ser Phe Glu Tyr
    130                 135                 140

Lys Val Lys Lys Met Val Leu Gln Glu Arg Ile Asp Asn Val Leu Lys
145                 150                 155                 160

Gln Gly Leu Val Arg
            165

(2) INFORMATION FOR SEQ ID NO:13:

(i) SEQUENCE CHARACTERISTICS:
        (A) LENGTH: 165 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:13:

Met Lys Asn Ala Leu Ile Ala Lys Ser Leu Leu Thr Leu Ala Ala Ile

```
            1               5                  10                 15
Gly Ile Thr Thr Thr Ile Ala Ser Thr Ala Asp Ala Ser Glu Gly
                    20              25              30

Tyr Gly Pro Arg Glu Lys Lys Pro Val Ser Ile Asn His Asn Ile Val
                35              40              45

Glu Tyr Asn Asp Gly Thr Phe Lys Tyr Gln Ser Arg Pro Lys Phe Asn
 50                      55                  60

Ser Thr Pro Lys Tyr Ile Lys Phe Lys His Asp Tyr Asn Ile Leu Glu
 65                  70              75                      80

Phe Asn Asp Gly Thr Phe Glu Tyr Gly Ala Arg Pro Gln Phe Asn Lys
                    85              90              95

Pro Ala Ala Lys Thr Asp Ala Thr Ile Lys Lys Glu Gln Lys Leu Ile
                100             105             110

Gln Ala Gln Asn Leu Val Arg Glu Phe Glu Lys Thr His Thr Val Ser
                115             120             125

Ala His Arg Lys Ala Gln Lys Ala Val Asn Leu Val Ser Phe Glu Tyr
 130                     135                 140

Lys Val Lys Lys Met Val Leu Gln Glu Arg Ile Asp Asn Val Leu Lys
145                 150             155                     160

Gln Gly Leu Val Lys
                165
```

(2) INFORMATION FOR SEQ ID NO:14:

(i) SEQUENCE CHARACTERISTICS:
        (A) LENGTH: 136 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:14:

```
Ser Glu Gly Tyr Gly Pro Arg Glu Lys Lys Pro Val Ser Ile Asn His
 1               5                  10                  15

Asn Ile Val Glu Tyr Asn Asp Gly Ser Phe Lys Tyr Gln Ser Arg Pro
                20                  25              30

Lys Phe Asn Ser Thr Pro Lys Tyr Ile Lys Phe Lys His Asp Tyr Asn
             35              40              45

Ile Leu Glu Phe Asn Asp Gly Thr Phe Glu Tyr Gly Ala Arg Pro Gln
 50                      55                  60

Phe Asn Lys Pro Ala Ala Lys Thr Asp Ala Thr Ile Lys Lys Glu Gln
 65                  70              75                      80

Lys Leu Ile Gln Ala Gln Asn Leu Val Arg Glu Phe Glu Lys Thr His
                 85                  90              95

Thr Val Ser Ala His Arg Lys Ala Gln Lys Ala Val Asn Leu Val Ser
             100             105             110

Phe Glu Tyr Lys Val Lys Lys Met Val Leu Gln Glu Arg Ile Asp Asn
             115             120             125

Val Leu Lys Gln Gly Leu Val Arg
 130                     135
```

(2) INFORMATION FOR SEQ ID NO:15:

(i) SEQUENCE CHARACTERISTICS:
        (A) LENGTH: 177 amino acids
        (B) TYPE: amino acid
        (C) STRANDEDNESS: single -continued

```
        (D) TOPOLOGY: linear (ii) MOLECULE TYPE: protein (xi) SEQUENCE DESCRIPTION: SEQ ID NO:15:

Ala Ser Gln Tyr Gly Pro Arg Pro Gln Phe Asn Lys Thr Pro Lys Tyr
1               5                   10                  15

Val Lys Tyr Arg Asp Ala Gly Thr Gly Ile Arg Glu Tyr Asn Asp Gly
            20                  25                  30

Thr Phe Gly Tyr Glu Ala Arg Pro Arg Phe Asn Lys Pro Ser Glu Thr
        35                  40                  45

Asn Ala Tyr Asn Val Thr Thr His Ala Asn Gly Gln Val Ser Tyr Gly
    50                  55                  60

Ala Arg Pro Thr Tyr Lys Lys Pro Ser Glu Thr Asn Ala Tyr Asn Val
65              70                  75                  80

Thr Thr His Ala Asn Gly Gln Val Ser Tyr Gly Ala Arg Pro Thr Gln
            85                  90                  95

Asn Lys Pro Ser Glu Thr Asn Ala Tyr Asn Val Thr Thr His Gly Asn
            100                 105                 110

Gly Gln Val Ser Tyr Gly Ala Arg Gln Ala Gln Asn Lys Pro Ser Lys
            115                 120                 125

Thr Asn Ala Tyr Asn Val Thr Thr His Ala Asn Gly Gln Val Ser Tyr
        130                 135                 140

Gly Ala Arg Pro Thr Tyr Lys Lys Pro Ser Lys Thr Asn Ala Tyr Asn
145                 150                 155                 160

Val Thr Thr His Ala Asp Gly Thr Ala Thr Tyr Gly Pro Arg Val Thr
            165                 170                 175

Lys
```